US011857810B2

(12) United States Patent
Aviad et al.

(10) Patent No.: US 11,857,810 B2
(45) Date of Patent: Jan. 2, 2024

(54) SYSTEM AND METHODS OF TISSUE MICROABLATION USING FRACTIONAL TREATMENT PATTERNS

(71) Applicant: LUMENIS LTD., Yokneam (IL)

(72) Inventors: Idan Aviad, Kiryat Haim (IL); Yoni Iger, Yokneam Ilit (IL); Assaf Gelstein, Yokneam Ilit (IL); A. Jason Mirabito, Newmarket, NH (US); Omer Peled, Haifa (IL)

(73) Assignee: LUMENIS BE LTD., Yokneam (IL)

( * ) Notice: Subject to any disclaimer, the term of this patent is extended or adjusted under 35 U.S.C. 154(b) by 249 days.

(21) Appl. No.: 17/175,886

(22) Filed: Feb. 15, 2021

(65) Prior Publication Data
US 2021/0290984 A1   Sep. 23, 2021

Related U.S. Application Data

(63) Continuation of application No. 15/803,763, filed on Nov. 4, 2017, now Pat. No. 10,953,245, which is a
(Continued)

(51) Int. Cl.
*A61B 18/20* (2006.01)
*A61N 7/00* (2006.01)
*A61B 18/00* (2006.01)

(52) U.S. Cl.
CPC .............. *A61N 7/00* (2013.01); *A61B 18/203* (2013.01); *A61B 2018/00029* (2013.01);
(Continued)

(58) Field of Classification Search
CPC ............ A61B 18/18; A61B 2018/1807; A61B 2018/1815; A61B 18/20; A61B 18/203;
(Continued)

(56) References Cited

U.S. PATENT DOCUMENTS

| 5,501,680 A | 3/1996 | Kurtz et al. |
| 5,885,211 A | 3/1999 | Eppstein |

(Continued)

FOREIGN PATENT DOCUMENTS

| EP | 2246095 | 11/2010 |
| WO | 9904709 | 2/1999 |

(Continued)

OTHER PUBLICATIONS

Partial European Search Report—Corresponding European Application No. 11751268, dated Mar. 31, 2017, 5 pages.
(Continued)

*Primary Examiner* — Ahmed M Farah
(74) *Attorney, Agent, or Firm* — ISUS INTELLECTUAL PROPERTY PLLC; Anthony Jason Mirabito

(57) ABSTRACT

An apparatus for treating tissue includes a first energy application device to direct energy at tissue of a patient to cause at least one channel to be formed and a controller to control application of energy from the first energy application device to form the at least one channel. The at least one channel may be in the shape of a spiral-like shape or may be in a flower-like shape. Mechanisms are provided to help open channels formed in the human skin structure. A second energy application source may be used to maintain the channel open after formation. The controller may cause the first energy application device to form a plurality of channels of varying depth, width and distribution over the human skin surface. The apparatus to control the application of energy may be operated using a foot-activated pedal.

6 Claims, 19 Drawing Sheets

Related U.S. Application Data continuation of application No. 13/038,773, filed on Mar. 2, 2011, now Pat. No. 9,993,664.

(60) Provisional application No. 61/439,056, filed on Feb. 3, 2011, provisional application No. 61/310,254, filed on Mar. 3, 2010, provisional application No. 61/310,239, filed on Mar. 3, 2010, provisional application No. 61/310,256, filed on Mar. 3, 2010, provisional application No. 61/310,249, filed on Mar. 3, 2010.

(52) U.S. Cl.
CPC ............... *A61B 2018/0047* (2013.01); *A61B 2018/00452* (2013.01); *A61B 2018/00613* (2013.01); *A61B 2018/00994* (2013.01); *A61B 2218/007* (2013.01); *A61N 2007/0034* (2013.01)

(58) Field of Classification Search
CPC .. A61B 2018/2035; A61B 2018/20351; A61B 2018/20353; A61B 2018/20355; A61B 2018/00315; A61B 2018/00452; A61B 2018/00458; A61B 2018/00464; A61B 2018/0047; A61B 2018/00571; A61B 2018/00577; A61B 2018/00636; A61B 2018/00642; A61B 2018/00648; A61B 2018/00696; A61B 2018/00702; A61B 2018/00738; A61N 7/00; A61N 7/0004; A61N 7/0034
USPC .............. 606/9–12; 604/19, 20, 22; 128/898
See application file for complete search history.

(56) References Cited

U.S. PATENT DOCUMENTS

| | | |
|---|---|---|
| 6,537,269 B1 | 3/2003 | Abe |
| 6,589,191 B2 | 7/2003 | Desinger |
| 6,692,456 B1 | 2/2004 | Eppstein |
| 7,331,953 B2 | 2/2008 | Manstein |
| 8,287,483 B2 | 10/2012 | Mitragotri et al. |
| 8,496,696 B2* | 7/2013 | Lemberg ............. A61B 18/203 607/89 |
| 8,778,002 B2* | 7/2014 | Moy ................... A61M 35/003 607/88 |
| 9,993,664 B2 | 6/2018 | Aviad |
| 2001/0016732 A1 | 8/2001 | Tobart et al. |
| 2001/0020166 A1 | 9/2001 | Daly et al. |
| 2002/0169394 A1 | 11/2002 | Eppstein et al. |
| 2003/0083607 A1 | 5/2003 | Bobo, Jr. |
| 2003/0216719 A1* | 11/2003 | Debenedictis ....... A61B 18/203 606/10 |
| 2005/0222565 A1 | 10/2005 | Manstein |
| 2008/0071258 A1* | 3/2008 | Lemberg ............. A61B 18/203 128/898 |
| 2008/0161782 A1* | 7/2008 | Chan .................... A61K 31/375 514/474 |
| 2008/0234626 A1* | 9/2008 | Chelak ................. A61N 1/0424 604/20 |
| 2009/0036914 A1 | 2/2009 | Houser |
| 2009/0069741 A1* | 3/2009 | Altshuler ............... A61B 5/441 606/33 |
| 2009/0171327 A1 | 7/2009 | Kurtz et al. |
| 2010/0082019 A1* | 4/2010 | Neev .................... A61B 18/203 604/23 |
| 2011/0230870 A1* | 9/2011 | Moy ................... A61M 35/003 606/9 |
| 2016/0095660 A1* | 4/2016 | Choye ................. A61B 18/203 606/9 |

FOREIGN PATENT DOCUMENTS

| | | |
|---|---|---|
| WO | 200033912 | 6/2000 |
| WO | 200123032 | 4/2001 |
| WO | 2007064718 | 6/2007 |
| WO | 2009/104530 | 8/2009 |

OTHER PUBLICATIONS

Search Report—Corresponding European Application No. 11751268, dated Aug. 15, 2017, 16 pages.

Search Report—Corresponding PCT Application—dated Nov. 24, 2011.

* cited by examiner

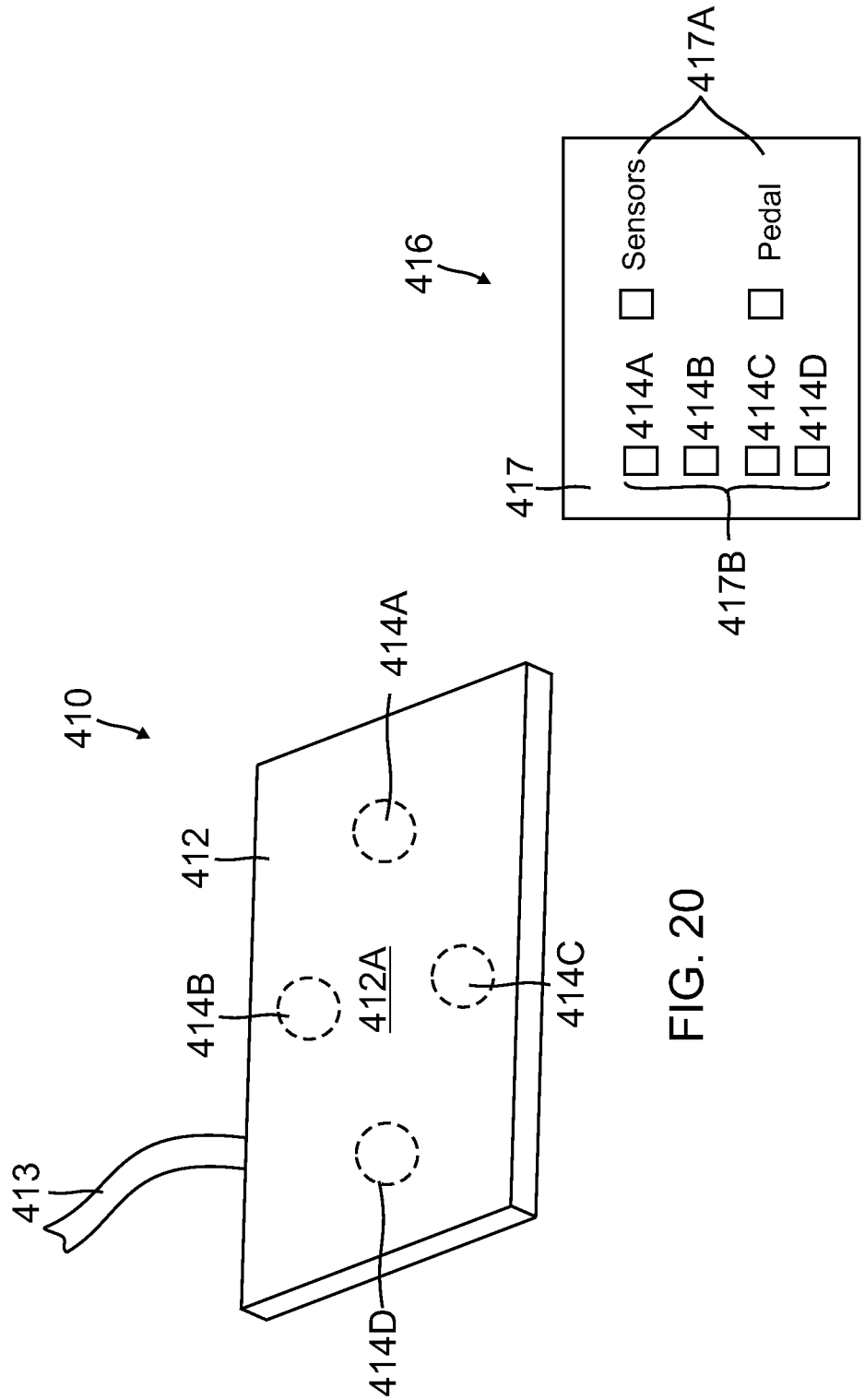

SYSTEM AND METHODS OF TISSUE MICROABLATION USING FRACTIONAL TREATMENT PATTERNS

RELATED APPLICATIONS

This application is a continuation application of U.S. application Ser. No. 15/803,763, filed Nov. 4, 2017, which is a continuation application of U.S. application Ser. No. 13/038,773, filed Mar. 2, 2011, now U.S. Pat. No. 9,993,664, issued on Jun. 12, 2018, which relates to and claims priority to: U.S. Application No. 61/310,239, filed on Mar. 3, 2010, entitled "Apparatus and Method for Microablation of Tissue and For Maintaining Formed Microchannels Open"; U.S. Application No. 61/310,249, filed on Mar. 3, 2010, entitled "System and Method of Laser Microablation of Tissue"; U.S. Application No. 61/310,254, filed on Mar. 3, 2010, entitled "Methods of Microablation of Tissue and Microablating Patterns"; U.S. Application No. 61/310,256, filed on Mar. 3, 2010, entitled "Footswitch for Activation and Dynamic Control of Light-Based Microablation System or Device and Tissue Ablation Parameters", and U.S. Application No. 61/439,056, filed on Feb. 3, 2011, entitled "System and Methods of Tissue Microablation Using Fractional Treatment Patterns", the entireties of which are incorporated by reference herein.

FIELD OF THE INVENTION

A system and methods of laser microablation provide selection and control of the distribution, densities and patterns of treatment "spots" and resulting macro-spots and microchannels created in human tissue for treatment of various skin and tissue conditions and pathologies.

The invention also provides a method of microablating tissue with a pattern of microchannels in which certain microchannels define a given depth and diameter to achieve a particular purpose. More particularly, the method forms superficial microchannels to help to provide mechanical support to and to prevent flow of fluids into, and out of, proximate deep microchannels. The method of the invention also helps deep microchannels retain an open structure during tissue treatment.

The present disclosure also relates to an apparatus and method for creating microablated channels in skin and for maintaining such microablated channels, once formed, open. The present disclosure is further directed to treating subsurface tissue through the channels created.

A system and method of laser microablation is disclosed which also provides selection and control of the distribution, densities, and actual impact of microchannels or treatment "spots" created in subsurface tissue that permits customized impacts, including for instance ablation-coagulation ratio, with respect to treatment type, tissues targeted, and skin and tissue characteristics and pathologies.

The invention also discloses and provides a mode of control, e.g., active, employing a foot activated control device for integration with a light-based ablation system or device that provides operator selection and control of modes of operation of the system or device, and selection and dynamic control of ablation treatment parameters.

BACKGROUND

Prior art laser systems are configured to produce sufficient energy to reach tissue ablation thresholds having fluence levels of about 5 J/cm$^2$, and to create a variety of treatment spot sizes on the order of from about 120 um to about 2 mm Such laser systems are powerful, producing high peak-power of up to about 280 W and up to about 222 mJ/pulse. In addition, these laser systems can deliver a range of ablative fractional treatment patterns with high-energy, short pulse scanning to form small, deep microablative treatment spots and large, superficial treatment spots, and combinations of both spot types. However, single laser systems with low power, capable of producing peak-power of up to about 40 W, and a limited range of working parameters may reach tissue ablation thresholds with only a certain maximum spot size above which tissue ablation cannot be achieved. Where treatment conditions or pathologies warrant scanning large areas of tissue, such single laser systems are inefficient and not effective. Thus, it is desirable for a low-power laser system and corresponding methods of ablative fractional treatment to produce fractional macro-spots that are comparatively larger than a maximum single laser spot size and can effectively ablate tissue for the apparatus described with reference to the description of the embodiments of FIG. 3 to FIG. 12B herein. Otherwise, the inventions of the present application are applicable to both lower power and high power devices. It is also desirable to provide a laser system and corresponding fractional treatment methods that produce macro-spots comprising impacts of micro-spots and micro-lines, while maintaining intact tissue between micro-spots and micro-lines, to thereby effectively create a fractional pattern within a fractional pattern.

SUMMARY OF THE INVENTION

In one aspect, an apparatus for treating tissue is disclosed. The apparatus includes a first energy application device to direct energy at tissue of a patient to cause at least one channel to be formed; a second energy application device to direct energy at the tissue of the patient to prevent the at least one channel from substantially closing; and a controller to: control application of energy from the first energy application device to form the at least one channel, and control application of energy from the second energy application device to the at least one channel to prevent the at least one channel from substantially closing for at least a pre-determined interval of time. The first and the second energy application devices may include the same devices.

In another aspect, the second energy application device includes a fluid source; and a pump to pressure fluid from the fluid source towards the at least one channel.

Further, the pump is configured to: create a vacuum external to the at least one channel to remove at least some of the fluid directed into the at least one channel.

Further, the fluid of the fluid source includes one or more of: gas, enhancing fluid to enhance the effect of laser energy transmitted through the pressurized enhancing fluid, and medicinal fluid.

In yet another aspect, the second energy application device includes a controllable ultrasound device to apply ultrasound energy in a direction substantially parallel to a longitudinal axis of the at least one channel to generate standing waves of varying amplitude to cause varying elasticity levels of the tissue.

The second energy application device may include a controllable energy application device to generate one or more standing waves over the at least one channel to elevate the Young modulus of the tissue.

The at least one channel may include a plurality of channels, and the controllable energy application device to generate the one or more standing waves may include a controllable energy application device to generate one or more standing waves having wavelengths based on a distance between at least two of the plurality of channels.

The second energy application device may also include a controllable ultrasound device to apply ultrasound energy in a direction along the tissue of a patient perpendicular to a longitudinal axis of the at least one channel to elevate the effective Young Modules of the tissue of the patient.

In another aspect, the apparatus for treating tissue includes a first energy application device to direct energy at a selected tissue surface of a patient to cause at least one channel to be formed; a controller to: control one or more parameters of application of energy from the first energy application device to form, and the controller further causing the first energy application device to form more than one channel on the selected skin surface of a patient, the distribution of the more than one channel being non-uniform over the skin surface.

The more than one channel formed may vary in depth of penetration into the skin surface of the human.

The time rate of the first energy application device forming the more than one channel may be determined by the rate of travel of the first energy application device over the skin surface.

Further, the controller is operatively connected to one of a manually or a foot operated device to control the application of the first energy application device. The controller may include a manual or foot operated device to apply energy to the selected tissue with a selected randomly determined density.

In another aspect, a sensor on the first energy application device may be connected to the controller and senses the rate of travel of the first energy application device and signals the controller to cause the first energy application device to form the more than one channel.

In another aspect, the channels formed may all be of one depth into the skin surface, or are of varying depth into the skin surface. The depth may be controlled by the controller in response to sensing the position of the first energy application device on the skin surface by a sensor device in the first energy application device.

Further, the density of the more than one channel on the skin surface may be controlled by the controller in response to sensing the position of the first energy application devices on the skin surface by a sensor device operatively associated within the first energy application device.

In another embodiment, an apparatus for treating tissue, may include a first energy application device to direct energy at tissue of a patient to cause at least one channel to be formed; a controller to: control application of energy from the first energy application device to form the at least one channel, and the controller may control the application of energy in response to the activation of a foot-operated device operatively connected to the controller.

Further, the foot-operated device may include foot-activateable devices to control one or more of the parameters: time intervals between activation of the first energy application device; the amount of energy delivered to the first energy activation devices; the depth of the channels formed; the distribution of the channels formed on the skin surface; and the width of the channels formed.

Each of the foregoing parameters may be controlled by a separate sensor device mounted on the foot-operated device and at least one of the sensors controlling the parameters may be variably activateable.

In yet another embodiment, an apparatus for treating tissue, may include a first energy application device to direct energy at tissue of a patient to cause at least one channel to be formed; a controller to: control application of energy from the first energy application device to form the at least one channel, the controller applying energy from the first energy application device to form a central channel; and the controller further applying energy from the first energy application device to form one or more secondary channels in the vicinity of the center channel.

The one or more secondary channels may be spaced a predetermined distance from the central channel.

The one or more secondary channels may substantially abut the central channel periphery. The one or more secondary channels may be arranged in any configuration and substantially surround the central channel.

The central channel may be of depth X and the one or more secondary channels are of depth $A<X$.

The diameter of the central channel and the one or more secondary channels may be of substantially the same diameter.

The diameter of the central channel may be X and the diameter of the one or more secondary channels is $x>X$.

In yet a further embodiment, an apparatus for treating tissue may include a first energy application device to direct energy at a tissue surface of a patient to cause at least one channel to be formed; a controller to: control application of energy from the first energy application device to form the at least one channel, and the controller forming the at least one channel in the shape of a decreasing spiral.

One or more of: depth of the channel, width of the channel, and distance between adjacent channels may be controlled by the controller.

More than one decreasing spiral may be formed on the skin of a patient within a predetermined skin area.

The controller may cause the first energy application device to form at least one micro-spot within the decreasing spiral channel.

The controller may cause the first energy application device to form at least one micro-spot outside of the at least one channel.

The decreasing spiral may be formed in at least one of the following shapes:

triangular; rectangular; square; and hexagonal.

Further, the controller may cause the first energy application device to produce at least one channel having an area of ablation, followed by an area of coagulation followed by an area of thermal heating.

The first energy application device may be one of a $CO_2$, an Er:YAG, an Nd:YAG; an Er:GHss Ulium laser operating in one of a continuous wave mode and a pulsed mode.

The depth of the channel may be varied by the controller along the decreasing spiral formed by the first energy application device.

Details of one or more implementations are set forth in the accompanying drawings and in the description below. Further features, aspects, and advantages will become apparent from the description, the drawings, and the claims.

BRIEF DESCRIPTION OF DRAWINGS

FIG. 20 is a schematic perspective illustration of a footswitch according to the invention for operation of a light-based tissue ablation system or device; and FIG. 21 is a schematic illustration of a user interface for use in selecting and enabling ablation parameter controls integrated with the footswitch shown in FIG. 20.

DETAILED DESCRIPTION

Figure 1:
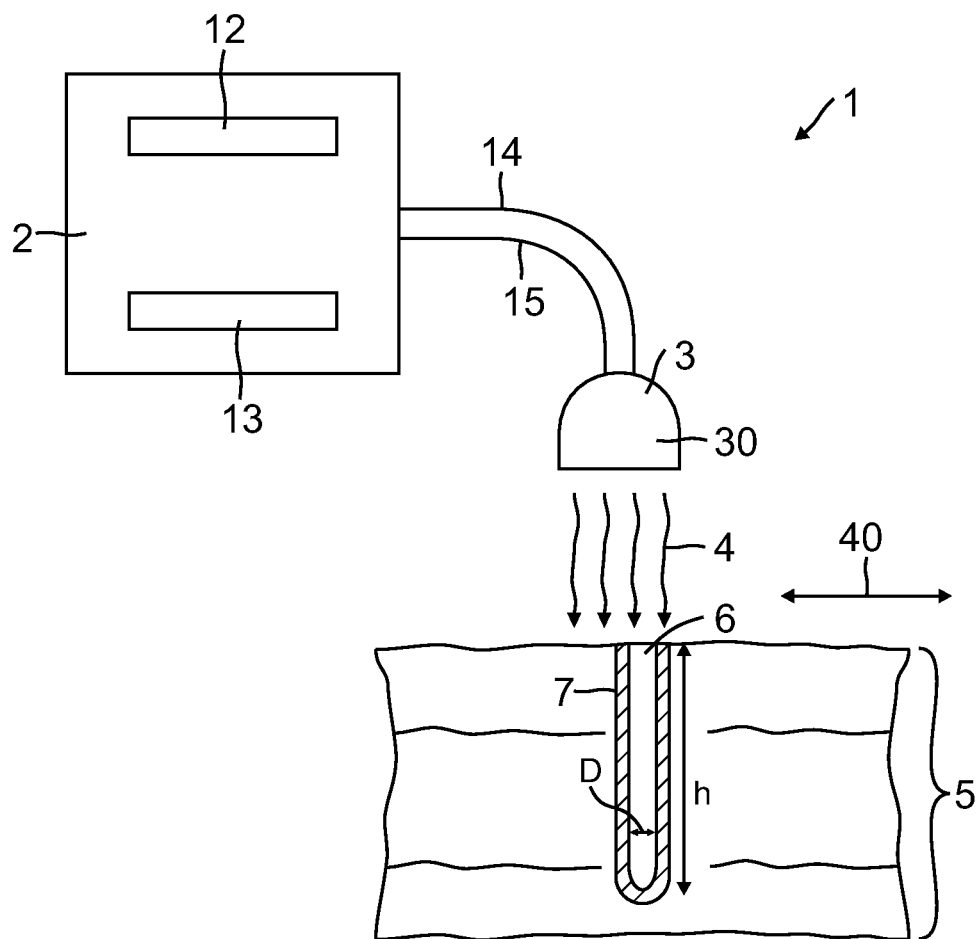
FIG. 1 is a schematic illustration of a microablation system according to one aspect of the invention, and a schematic illustration of a treatment spot or microchannel created in tissue as a result of microablation produced with the system.

The invention provides a system and methods for treating tissue using electromagnetic radiation and microablation techniques. Such a system and microablation techniques form microchannels through a surface of tissue to treat subsurface tissue for any of a number of skin conditions and pathologies. The tissue ablation system according to the invention includes a laser unit and a laser emitting device for ablating microchannels in tissue, such as the system disclosed in assignee's co-pending patent application Ser. No. 11/730,017, filed Mar. 29, 2007 and entitled "System and Method of Microablation of Tissue" (Patent Publication No. 2008/0071258), the entirety of which is incorporated herein by reference. The laser emitting device includes a scanning device configured with a number of mirrors or alternatively a single mirror, or other reflective surfaces, disposed in an arrangement and at an orientation relative to one another such that the laser emitting device emits a laser beam in a given pattern of rays or beams. Software controls the scanning device to emit laser light in a desired beam pattern and/or beam profile to achieve specific treatment protocols. These types of scanning devices are disclosed in assignee's U.S. Pat. Nos. 5,743,902, 5,957,915, and 6,328,733, the entireties of which are incorporated herein by reference.

Alternatively, the scanning device may be or may include a laser beam splitter, which is constructed and arranged to deliver a given pattern of treatment radiation to produce multiple treatment areas or "spots." Such treatment "spots" create multiple microchannels in subsurface tissue that may be distributed in a pattern substantially throughout a tissue treatment area. For instance, using a laser beam splitter, ablation radiation may be varied to achieve a certain fractional pattern of spots along a treatment area to create microchannels having certain parameters, such as certain depths and diameters. The beam splitter may include a multi-lens plate having a plurality of lenses. Some lenses may be configured to focus ablation radiation more than other lenses, such that, some lenses sufficiently focus ablation radiation to penetrate the surface of tissue, while other lenses do not. The plurality of lenses may include lenses having varying size and focal length. The plurality of lenses may include a mechanism, e.g., an array of controllable filters or shutters, which may open or close the optical path, to or of, any single lens. The multi-lens plate thereby may create any fractional pattern of treatment macro-spots or lines that are drawn or created using any subset of lenses of the multi-lens plate. The invention is not limited to scanning laser beam splitters and envisions that other sophisticated stationary beam splitters may achieve the scanning function disclosed herein. For purposes of disclosing the invention, the term "scanner" or "scanning device" is used to refer to a scanning device in the laser emitting device as described with reference to FIG. 1 and to laser beam splitters, whether such beam splitters are stationary or portable.

In lieu of the scanning devices described above, a semiconductor device named DLP® and manufactured by Texas Instruments may be used in coordination with the laser of FIG. 1. With a laser unit 2, shown in FIG. 1, a DLP® semiconductor may be used to direct laser light to one or more of the hinged-mounted microscopic mirrors and then onto the human skin. DLP® is described in an article "How DLP Technology Works" and can be found at: www.dlp.com/technology/how-dlp-works/default.aspx.

Generally, the laser emitting device and the scanning device apply a laser beam to a tissue treatment area with a given emitted beam pattern such that treatment areas or "spots" and the resulting multiple microchannels are created with required or desired dimensions and are distributed throughout subsurface tissue in a required or desired pattern. The scanning device uses software designed and configured to change and to control treatment spots with respect to spot pattern, spot pattern size, spot size, spot shape, spot densities, and/or spot or ablated microchannel depth and pattern/sequence vs. randomized.

In one configuration according to the invention, a laser unit with a laser emitting device includes a scanning device and software to produce and emit a laser beam during scanning that creates multiple spots and microchannels in a randomized sequence. As the scanning device moves across a treatment area, the scanning device applies a laser beam as randomized treatment spots. Movement of the scanning device controls the distribution and density of the randomized treatment spots area across the treatment area. The distribution and density of the randomized treatment spots is also controlled by the number of repetitions of scanning across a given treatment area and the extent of scanning overlap in the treatment area.

In another configuration of the invention, a laser unit and a laser emitting device includes a scanning device and software to produce and emit a laser beam during scanning that creates multiple spots in a predetermined fractional pattern to thereby create microchannels along a tissue treatment area.

The scanning device and software according to the invention thereby enable controlled and intuitive treatment of tissue with more or less distribution and density of treatment spots along specific areas of a total treatment area. The scanning device and software thereby permit greater flexibility and control of microablative techniques.

Referring to FIG. 1, in one aspect, the invention provides a system for performing microscopic ablation or partial microablation of tissue to form one or more microchannels 6 through a surface of tissue to effect treatment within subsurface tissue. For instance, in skin tissue, proteins such as collagen reside in the dermal layer of the skin. Microchannels 6 described below may be used to target and alter collagen fibers within the skin dermis as an effective treatment of, for instance, wrinkles of the skin or cellulite. In another instance, microchannels 6 described below may be used to target and thermally treat portions of the skin dermis to coagulation at certain depths to thereby effectively treat undesirable skin pigmentation or lesions. Alternatively, microchannels 6 may create a passage through which targeted tissues may be treated, and/or through which material(s) may be extracted or material(s), such as medication, may be delivered to targeted tissues. Also, microchannels 6 may create a passage through targeted tissues through which a second laser beam having the same or different characteristics from beams forming such microchannels 6 may be supplied. In some embodiments of the invention, microchannels 6 may produce partial lateral denaturation of proteins, e.g., within walls and/or along bottoms of microchannels.

The tissue ablation system 1 includes a laser unit 2 and a laser emitting device 3 for ablating one or more microchannels 6 into tissue 5 for treatment. A microchannel 6 may include a hole, column, well, or the like created by ablating tissue 5 with a laser beam 4 which the laser emitting device 3 supplies. The laser emitting device 3 includes a scanning device 30 for emitting ablation radiation in a given fractional pattern of treatment "spots." As used to disclose the invention, treatment "spot" refers to an ablated area created by laser radiation and/or a microchannel 6 that results from such ablation.

The laser unit 2 may further include a controller 12 programmed and configured to control the laser emitting device 3. The laser unit 2 may also include an input interface 13 capable of receiving input parameters from a user of the system 1. The controller 12 may provide the laser emitting device 3 with a command, via one or more signals 14 to the laser unit 2, for applying a pulse or a series of pulses to tissue 5 for treatment.

The system 1 illustrated in FIG. 1 is a typical configuration and arrangement of a $CO_2$ laser system in which a $CO_2$ laser is included in the laser unit 2, and an arm or optic fiber 15 delivers a laser beam 4 to the laser emitting device 3. Alternatively, the system 1 may include a YAG or Erbium laser system that includes an Erbium laser that may be housed within the scanner 30 or a hand piece. Other laser systems with the power to form microchannels may also be utilized.

With further reference to FIG. 1, applying laser radiation to tissue with the laser unit 2 creates one or more microchannels 6 in subsurface tissue and may also cause tissue surrounding the microchannels 6 to dissipate heat resulting from the heating and evaporating of tissue that creates the microchannels 6. As a result, a thermally-affected or residual heating zone 7 may form in surrounding walls and/or bottoms of the microchannels 6. The residual heating zone 7 is generally indicative of damaged tissue and tissue necrosis, or, in particular, cell death. As used to disclose the invention, "damaged" means inducing cell death in one or more regions of the dermal tissue of interest, or stimulating the release of cytokines, heat shock proteins, and other wound healing factors without stimulating necrotic cell death.

In addition, treatment spots or microchannels 6 may include exclusively one type of microchannel 6 or a combination of different types of microchannels 6. For instance, formation of a combination of different types of microchannels 6 may include a first pattern of non-invasive, superficial microchannels 6 that do not have ablative effects, but only coagulate tissue, and a second pattern of invasive microchannels 6 that have ablative effects. Different types of microchannels 6 may be created in subsurface tissue using multiple lasers that apply laser radiation at different wavelengths in order to achieve different types of invasive and non-invasive, microchannels 6. Multiple lasers may be incorporated into a common optical axis and may share the same delivery mechanism(s).

Figure 2:
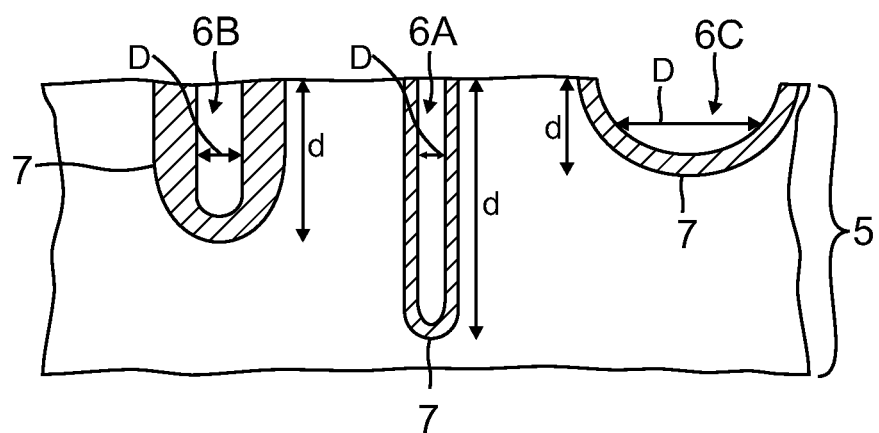
FIG. 2 is a cross-sectional illustration of different types of microchannels created with laser microablation techniques according to the invention.

Referring to FIG. 2 and with further reference to FIG. 1, various microchannels 6A, 6B and 6C are shown that are characterized by certain parameters including, but not limited to, microchannel diameter D and depth d. The energy and propagation characteristics of the laser beam applied to tissue 5 help to control the diameter D and depth d of the resulting microchannels 6A, 6B and 6C. Such energy may be pulsed laser or continuous wave laser and its propagation characteristics may include, but are not limited to, selected wavelength, power, and laser beam profile. Laser beam profile characteristics may include, but are not limited to, pulse width, pulse duration, pulse frequency, spot size and fluency. Further, volumes and profiles of residual heating zones 7 surrounding ablated areas are due to laser beam characteristics including, but not limited to, selected wavelength, individual pulse energy and fluence, energy of defined sequences of pulses, pulse duration, power distribution, and laser spot shape and size.

As shown in FIG. 2, microchannels 6A, 6B and 6C and residual heating zones 7 may vary within a single treatment session, such that, more than one type of treatment may be applied to a given tissue treatment area. For instance, a given laser beam profile may produce superficial treatment spots and microchannels 6B, or may produce deep, more invasive treatment spots and microchannels 6A. Another given laser beam profile may produce superficial and comparatively large, e.g., about 1.3 mm, macro treatment spots that create superficial and relatively wide microchannels 6C. Superficial microchannels 6B and 6C typically target comparatively superficial conditions and pathologies including, for instance, skin pigmentations, pigmented lesions and the like, while comparatively deep microchannels 6A typically target tissue collagen and stimulate cell growth. Combining deep and superficial treatment spots that vary with respect to spot size (diameter), spot depth, spot shape, spot density, and/or fractional pattern enables a more dynamic treatment protocol than may be achieved with a single type of microablative treatment.

Further, microchannels 6A, 6B and 6C may be created by applying laser radiation according to a random scanning sequence. Random scanning sequences may be achieved with software algorithms that configure sequential laser pulses, such that, one or more adjacent or subsequent laser pulses may be applied at a spot farthest from the spot of a prior laser pulse to define a predetermined fractional pattern of treatment spots. Sequencing of adjacent or sequential laser pulses helps allow treated tissue to cool between laser pulses.

As mentioned, the laser system 1 and/or laser unit 2 may employ software to configure laser beam profiles to deliver radiation to treatment areas in predetermined fractional spot patterns to create microchannels having specific parameters, as described above, to treat particular skin conditions and pathologies.

Macro-Spots and Microchannels

Figure 3A:
FIGS. 3A and 3B are illustrations of fractional patterns of treatment macro-spots having a snail-shaped pattern according to another aspect of the invention.
Figure 3B:
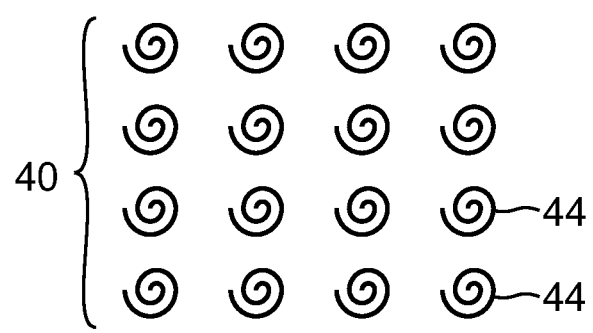

Referring to FIGS. 3A and 3B, in another aspect, the invention provides a method of tissue microablation that may employ the system 1 and/or laser unit 2 described above with reference to FIGS. 1 and 2 including a $CO_2$ laser to scan tissue treatment areas with ablative radiation to create comparatively large treatment spots or "macro-spots." Such macro-spots create shallow and relatively wide microchannels having configurations that are advantageous for scanning large tissue treatment areas. In this configuration of the system 1 and/or the laser unit 2, the $CO_2$ laser generates laser beams having an energy distribution or intensity approximating a particular beam profile to create a predetermined multiple macro-spots 42 and 44 within a given tissue treatment area 40. As shown in FIGS. 3A and 3B, a single macro-spot 42 and 44 results from scanning a $CO_2$ laser beam on a focal plane along the treatment area 40 in a circular or spiral scan pattern to create or draw a macro-spot 42 and 44 with a spiral- or coil-shaped pattern, referred to in this disclosure as a "snail-shaped" pattern.

Figure 4:
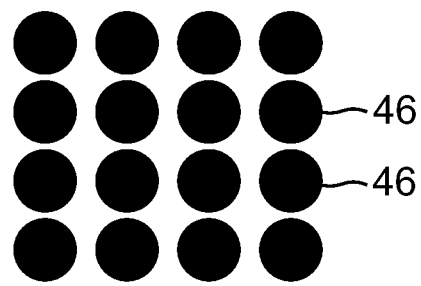
FIG. 4 is an illustration of a fractional pattern of treatment spots created by impact of a single beam.
Figure 3C:
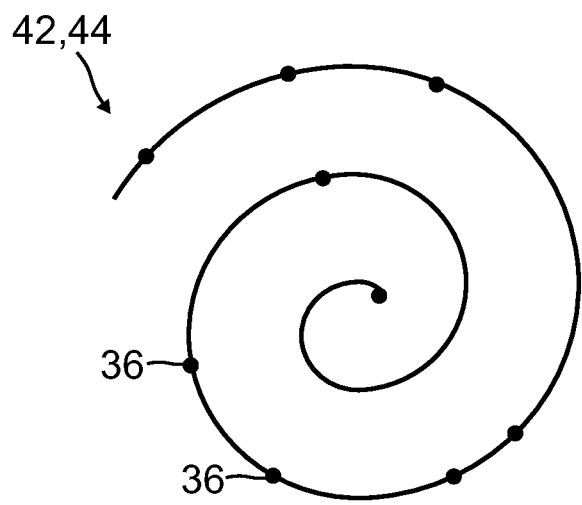
FIGS. 3C and 3D are illustrations of fractional patterns of micro-spots with a treatment macro-spot.
Figure 3D:
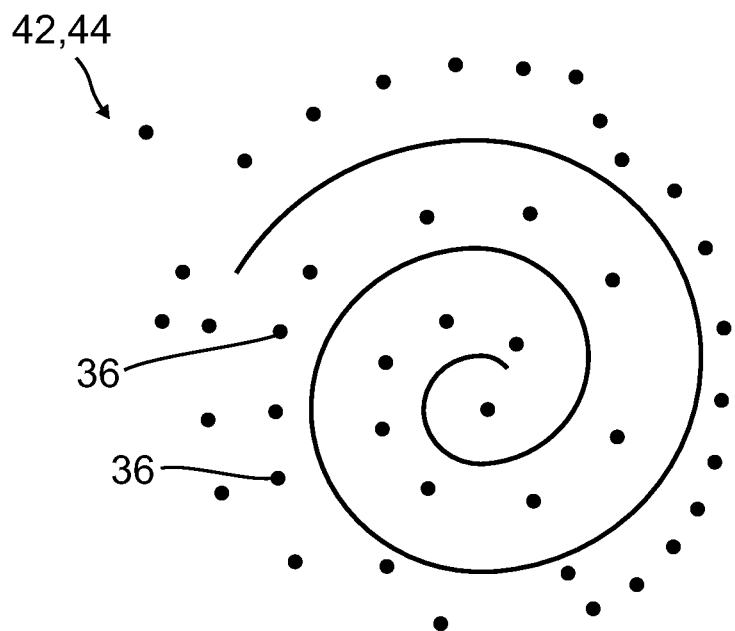

In a preferred embodiment of the invention, the $CO_2$ laser includes a beam diameter of about 120 um and operates in a continuous wave mode, irradiating a continuous scan line in a circular or spiral pattern to create or draw the snail-shaped pattern of the macro treatment spots 42 and 44. Referring to FIG. 4 and with further reference to FIGS. 3A and 3B, macro-spots 42 and 44 are large treatment spots relative to the micro treatment spots 46 shown in FIG. 4 and the microchannels 6A, 6B, and 6C shown in FIG. 2. Such micro-spots and corresponding microchannels result from scanning treatment areas with a laser in a pulsed mode that creates, with single or multiple pulses, single micro-spots and produces arrays of separate microchannels having potentially any of the general configurations illustrated in FIG. 2. The 120 um $CO_2$ laser may scan macro-spots 42 and 44 according to the invention with diameters of from about 200 um to about 2 mm, and preferably from about 700 um to about 1.4 mm. The system 1 and/or the laser unit 2 according to the invention may be configured to readily and quickly switch between a pulsed mode and a continuous mode of operation. Therefore, while drawing any continuous scan lines to create macro-spots, the system 1 and/or the laser unit 2 according to the invention can create any pattern of separate micro-spots 36 with any microchannel characteristics along the scan lines, as shown in FIG. 3C, or between the scan lines and/or between the macro-spots 42 and 44, as shown in FIG. 3D.

Figure 5A:
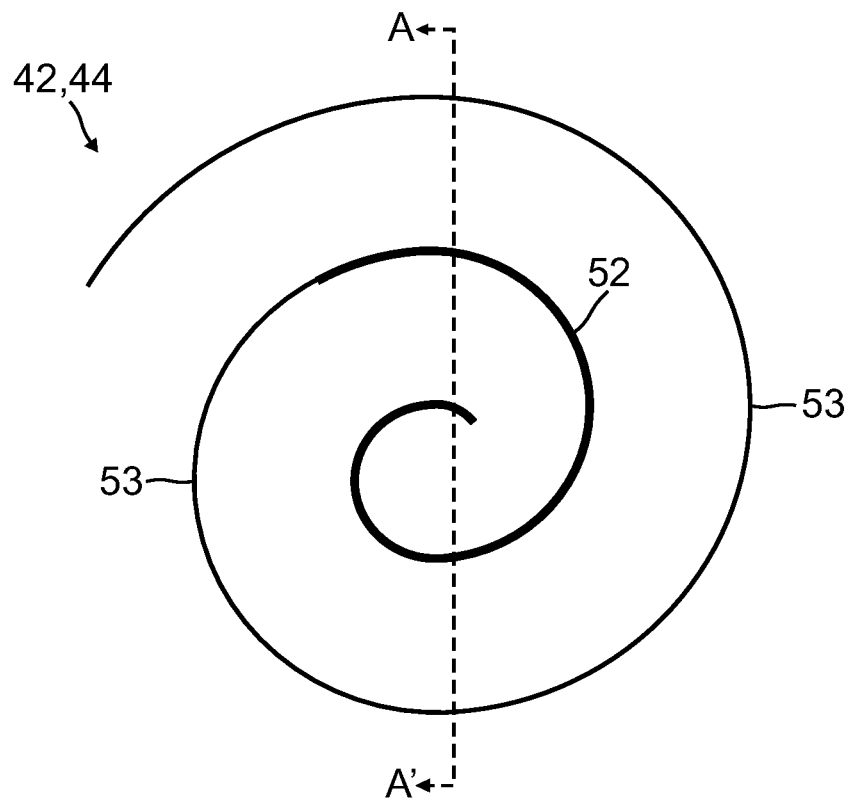
FIG. 5A is an illustration of a fractional pattern of a treatment macro-spot according to the invention.
Figure 5B:
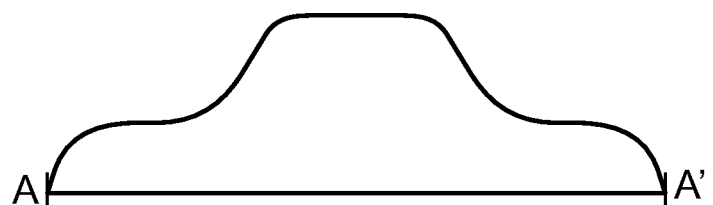
FIG. 5B is an illustration of energy distribution along a cross section of the treatment macro-spot shown in FIG. 5A.

Referring to FIGS. 5A and 5B and with further reference to FIGS. 3A and 3B, where the method according to the invention operates the $CO_2$ laser in continuous wave mode, the characteristics of the laser beam profile applied to treatment areas to scan macro-spots 42 and 44 may be controlled and varied before and/or during scanning to affect the energy levels and fluence applied along the spiral scan line that creates the snail-shaped macro-spot 42 and 44. Applying a particular beam profile in a continuous wave mode along the scan line can thereby result in relatively continuous or varying energy levels and fluence throughout the snail-shaped pattern. As a result of the controlled distribution of energy levels and fluence throughout the snail-shaped macro-spot 42 and 44, the resulting microchannel configurations may be controlled and may be varied depending on the treatment protocol and/or condition or pathology being treated. FIG. 5A is a top view of the snail-shaped pattern of a macro-spot 42 and 44 that illustrates higher fluence 52 applied at approximately about or along a center of the treatment spot 42 and 44 in comparison to fluence applied along marginal segments 53 and the periphery 53 of the snail-shaped pattern. Higher fluence segments 52 of the scan pattern would create deeper ablated portions within the resulting microchannel relative to those resulting from the lower fluence 53 segments. FIG. 5B illustrates an effective, cumulative energy distribution throughout the snail-shaped pattern along a cross-section of the macro-spot 42 and 44 shown in FIG. 5A taken at line A-A' that represents a beam profile that may have been applied to create the macro-spot 42 and 44 and the resulting microchannel using a single-beam, single-pulse laser or continuous laser, which may have been used to create the macro-spot and respective microchannel.

Figure 6A:
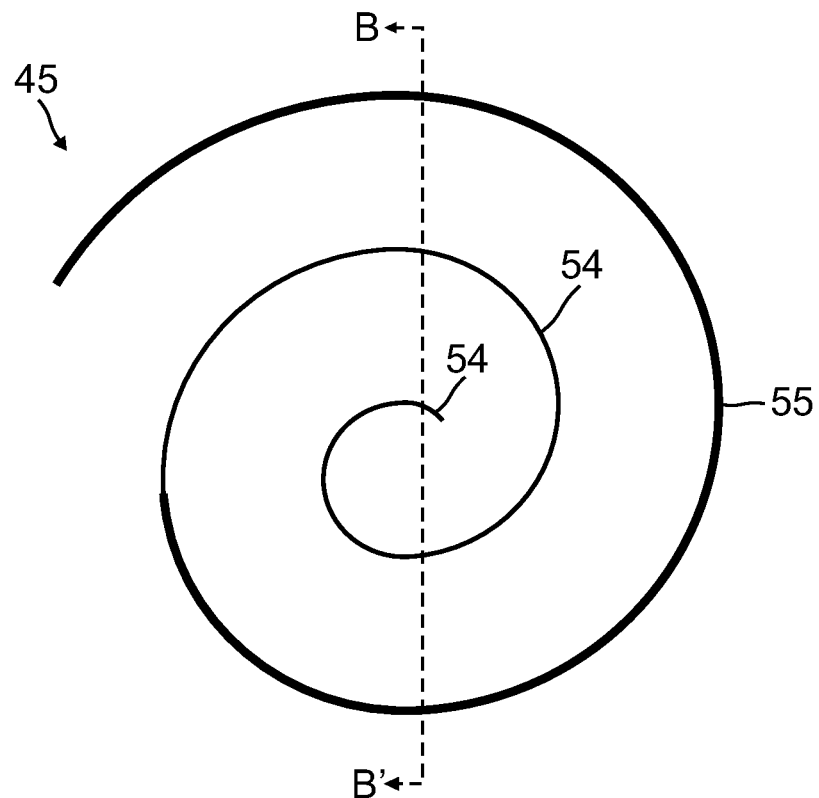
FIG. 6A is an illustration of a fractional pattern of a treatment macro-spot according to the invention.
Figure 6B:
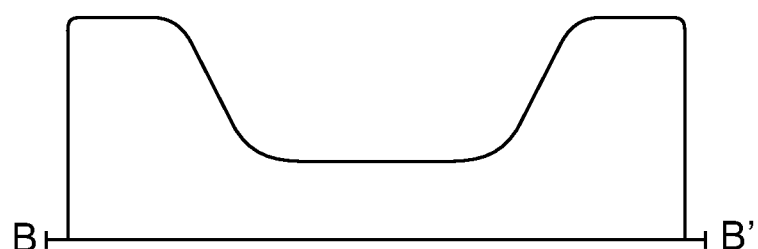
FIG. 6B is an illustration of energy distribution along a cross section of the treatment macro-spot shown in FIG. 6A.

Referring to FIGS. 6A and 6B, in contrast, other macro-spots 45 may be formed with different distributions of energy and fluence along the snail-shaped pattern. FIG. 6A is a top view of the snail-shaped pattern of a macro-spot 45 that illustrates lower fluence 54 applied at approximately about or along a center of the treatment spot 45 in comparison to fluence applied along marginal and peripheral segments 55 of the snail-shaped pattern. FIG. 6B illustrates an effective, cumulative energy distribution throughout the snail-shaped pattern along a cross-section of the macro-spot 45 shown in FIG. 6A taken at line B-B' that represents a beam profile applied to create the macro-spot 45 and resulting microchannel.

Figure 7A:
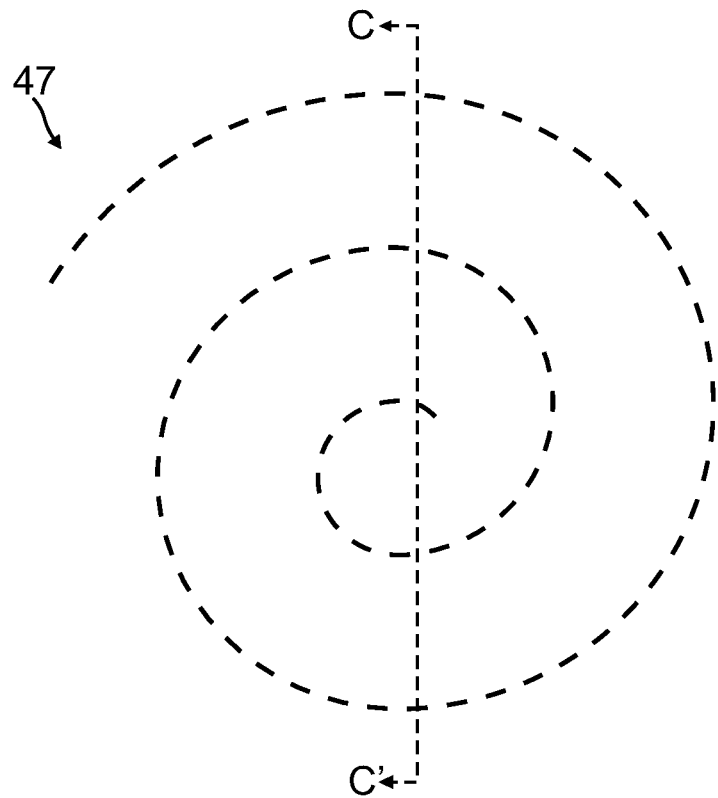
FIG. 7A is an illustration of a fractional pattern of a treatment macro-spot according to the invention.
Figure 7B:
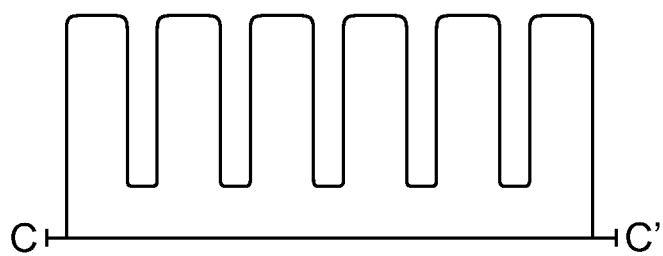
FIG. 7B is an illustration of energy distribution along a cross section of the treatment macro-spot shown in FIG. 7B.
Figure 8A:
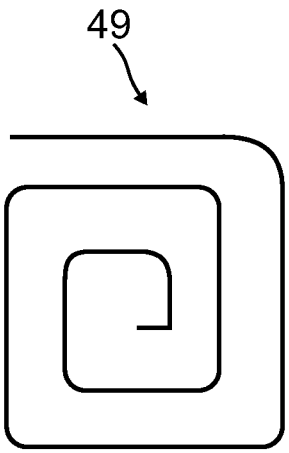
FIGS. 8A-8D are illustrations of other fractional patterns of treatment macro-spots according to the invention.
Figure 8B:
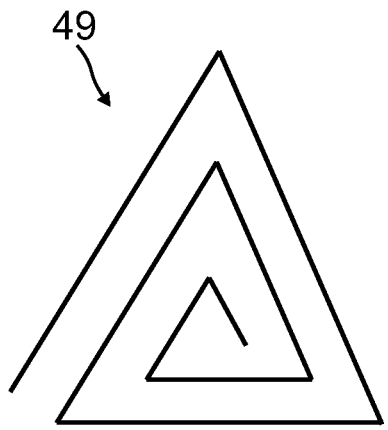
Figure 8C:
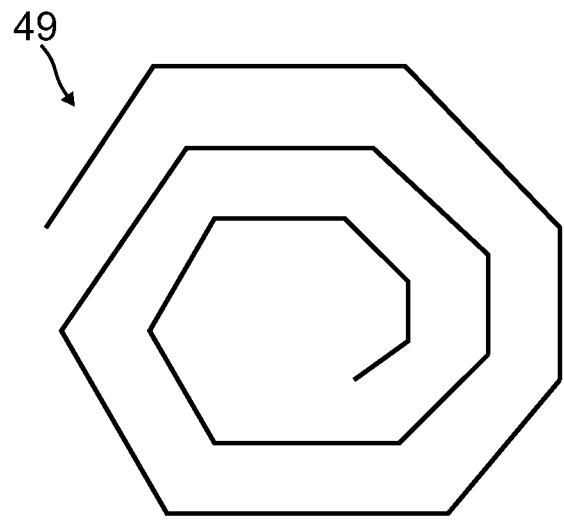
Figure 8D:
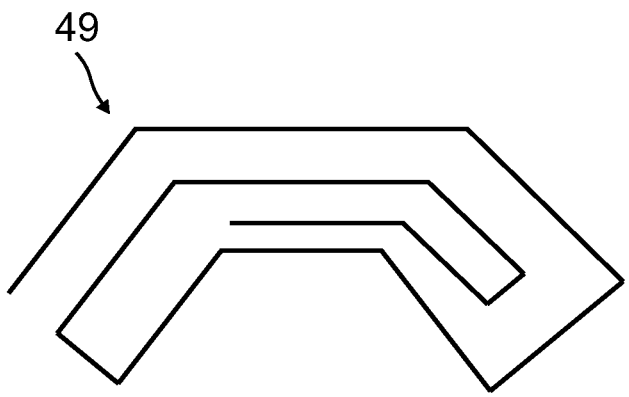

FIGS. 7A and 7B illustrate another configuration of the snail-shaped macro-spot 47 according to the invention created with intermittent scanning along the spiral scan line that draws the macro-spot 47 with a discontinuous snail-shaped pattern. In one configuration of the macro-spot 47 shown in FIG. 7A, the laser energy is alternately applied and withdrawn along the spiral scan line during continuous scanning to draw the discontinuous pattern. The intermittent applications of laser energy may be applied along the scan line for identical durations throughout scanning resulting in relatively even distributions of energy along the spiral scan line, or may be applied for varied durations such that segments of the scan line to which laser energy is applied are varied in length. FIG. 7B illustrates a potential cumulative energy distribution throughout the snail-shaped pattern along a cross-section of the macro-spot 47 shown in FIG. 7A taken at line C-C' that represents a beam profile.

The snail-shaped patterns of the macro-spots 42 and 44 shown in FIGS. 5A thru 7B illustrate the potential of the microablation method according to the invention to control and vary the energy levels and fluence throughout the snail-shaped macro treatment spot 42 and 44 before or during scanning to thereby create microchannels along treatment areas having required or desired parameters and configurations that may be advantageous toward optimizing a treatment protocol for a particular skin condition or pathology.

While the snail-shaped macro-spots 42 and 44 described above are created with circular spiral scanning patterns, the invention is not so limited and envisions other spiral patterns are possible for creating the shaped macro-spot 42 and 44. Referring to FIGS. 8A-8D, other possible alternative scanning patterns according to the invention are illustrated that do not include a circular spiral, but may include a rectangular-shaped, triangular-shaped and other shaped spiral pattern 49 as shown. Those of ordinary skill in the art will appreciate and anticipate other spiral shapes and profiles are possible to create the shaped pattern of the macro-spots.

With further reference to FIGS. 3A and 3B, the method according to the invention may control and vary the laser beam profile and scanning movement to create macro-spots spots 42 and 44 having a snail-shaped pattern with a given spread or density. As shown in FIG. 3A, some configurations of macro-spots 42 may have a snail-shaped pattern that is dense and less open, while other configurations of macro-spots 44 may have a snail-shaped pattern that is less dense and more open as shown in FIG. 3B. Control and variation of the spiral scanning movement of the laser beam helps to create the snail-shaped pattern with a required or desired spread or density, which is a direct result of the distance between successive snail pattern loops. In those configurations of the macro-spots 42 and 44 shown in FIGS. 3A and 3B, successive spiral loops are formed from a given center of the spiral scan line with a substantially consistent gradual increase in radii from the spiral scan line center to the pattern periphery, such that, distances between successive spiral loops within the pattern are substantially the same. Alternatively, successive spiral loops may be formed with gradually increasing or gradually decreasing radii from the spiral scan line center, such that, distances between successive spiral loops gradually increase or gradually decrease toward the pattern periphery. In addition, spiral loops may be formed with continuously increasing and decreasing radii from the spiral scan line center, such that, distances between spiral loops are inconsistent.

The microablative methods according to the invention, as well as the system 1 and/or laser unit 2 according to the invention, thereby enable control and adjustment of the spread or density of the snail-shaped pattern of each macro-spot 42 and 44, as well as control and adjustment of energy distributions and, in particular, energy levels and fluence applied along the spiral scan line that forms the snail-shaped pattern. The methods permit control and adjustment of these parameters prior to and/or during scanning treatments. The methods also provide flexibility in controlling and adjusting parameters of beam profiles in order to effective and final cumulative beam profiles are achieved that are specific to and advantageous for treatments of particular skin and tissue conditions or pathologies.

Figures 9A, 9B:
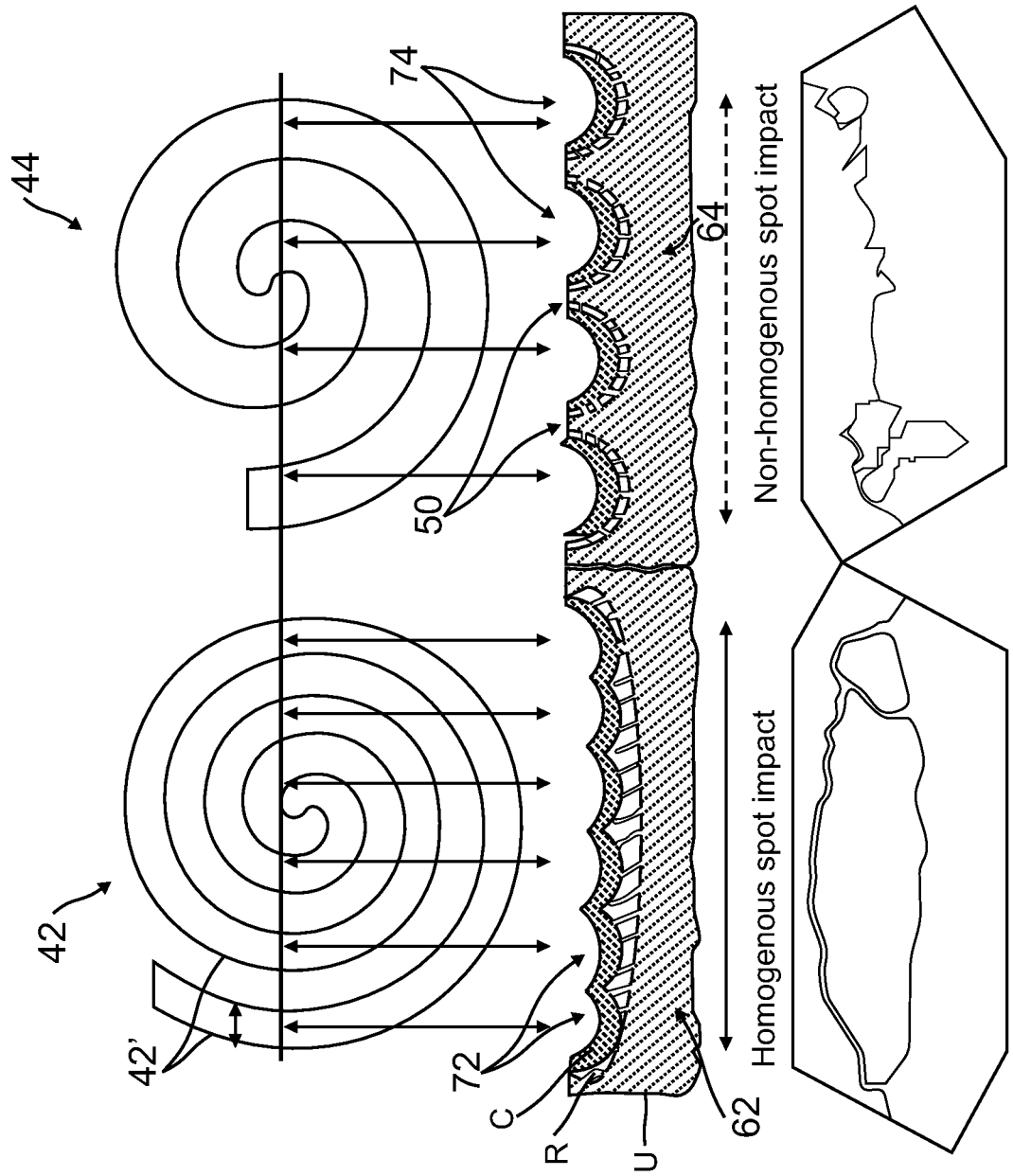
FIGS. 9A and 9B are cross-sectional illustrations of microchannels resulting in tissue from fractional patterns of macro-spots shown in FIGS. 3A and 3B.

Referring to FIGS. 9A and 9B, cross-sections of treated tissue are shown that illustrate the macro-spot impact and the tissue effects resulting from fractional treatment patterns of macro-spots 42 and 44 according to the invention. The spread or density of the snail-shaped pattern of the macro-spots 42 and 44 may be controlled to create dense or spread-out ablation zones 72 and 74. In addition, the density of the snail-shaped pattern of macro-spots 42 and 44 may be further controlled to affect the homogeneity of tissue ablation achieved within a given microchannel 62 and 64. As shown in FIG. 3A, spots 42 having a dense (compared to the pattern of FIG. 3B) snail-shaped pattern create microchannels 62 with a more homogeneous spot impact. In contrast, as shown in FIG. 3B, spots 44 having a less dense or more spread out snail-shaped pattern creates microchannels 64 with a non-homogenous spot impact.

More specifically, FIG. 9A shows the macro-spot 42 having a dense and less open snail-shaped pattern that creates a resulting microchannel 62 with a substantially homogeneous impact. The spiral loops 42' of the macro-spot 42 ablate areas of tissue 72 with a corresponding density, such that, the microchannel 62 includes a spot impact of substantially contiguous ablated zones 72. In contrast, FIG. 9B shows the macro-spot 44 having a more open snail-shaped pattern that creates the resulting microchannel 64 with a non-homogeneous impact. The spiral loops 44' of the macro-spot 44 ablate areas of tissue 74 with a corresponding density, such that, the microchannel 64 includes areas of undamaged tissue 50 between zones of ablated tissue 74. As mentioned, the spread or density of the spiral loops 42' and 44' of the macro-spots 42 and 44 controls the spot impact that results in certain configurations of the microchannels 62 and 64 at least in terms of homogeneity of ablation as shown here.

In addition, the spiral loops 42' and 44' of the snail-shaped patterns 42 and 44 create, such that, one fractional pattern of impact spots or ablated zones 72 and 74 is created within another fractional pattern of multiple microchannels 62 and 64 along a treatment area.

The macro-spots 42 and 44 shown in FIGS. 9A and 9B are presumed to have substantially consistent distributions of energy levels and fluence along the scan lines forming the snail-shaped patterns, such that, the ablated zones 72 and 74 within a single microchannel 62 and 64 have substantially similar depths and diameters. However, as described below with reference to FIGS. 12A and 12B, macro-spots that have varying energy levels and fluence along the spiral scan line forming the snail-shaped pattern would form ablated zones within a single microchannel having different depths and possibly different diameters.

As mentioned, relatively large macro-spots 42 and 44 are advantageous for treating large areas of tissue. The resulting microchannels 62 and 64 formed from the macro-spots 42 and 44 may be superficial, penetrating below the tissue surface to depths of from about 1 um to about 200 um, and may have the deepest points of the microchannels 62 and 63 approximately about the centers of the microchannel bottoms, depending on the energy levels and fluence applied along the spiral scan line drawing or creating the snail-shaped pattern. The sizes of the macro-spots 42 and 44 may create microchannels 62 and 64 having widths (diameters) of from about 200 um to about 2 mm.

Figure 10:
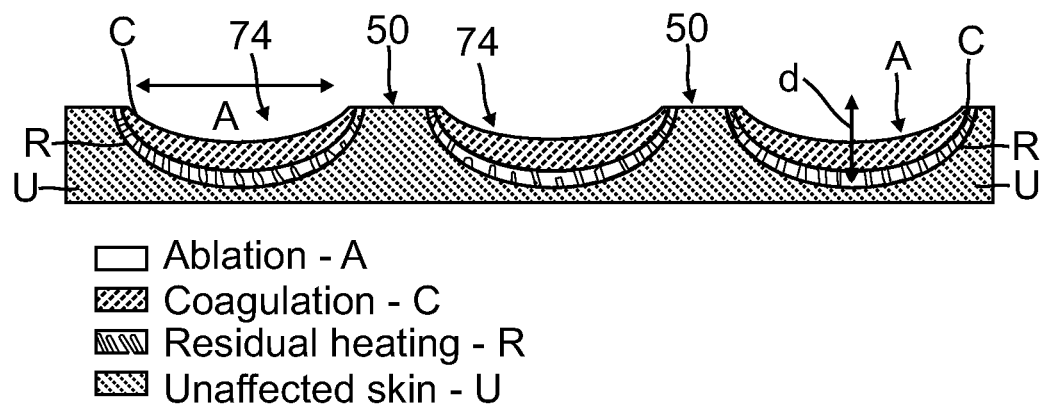
FIG. 10 is a cross-sectional illustration of a portion of the microchannel shown in FIG. 9B.

Referring to FIG. 10, a portion of the microchannel 64 shown in FIG. 9B illustrates the tissue effects resulting from microablative treatment with the macro-spot 44 patterns. The spot impact of the spiral loops of the macro-spot 44 are shown by the ablated zones 74, which are formed from heating or vaporizing tissue as a result of the energy levels and fluence applied along the spiral scan line of the snail-shaped pattern. Coagulation C zones and residual heating zones R may form within tissue surrounding the ablated zones 74 as a result of lower energy levels and fluence received along certain depths of the subsurface tissue. The microablation treatment pattern thereby preferentially heats tissues at certain required or desired depths below the tissue surface to effect treatment, while not affecting subsurface tissue not targeted for treatment, which remains undamaged tissue U. As described above, the macro-spot 44 having a less dense and open spiral scan line may result in areas of undamaged tissue 50 throughout the microchannel 64, such as between adjacent ablated zones 74. The spread or density of the spiral scan line can thereby help to control and vary the ratio of damaged tissue to undamaged tissue within a given microchannel, such that, the macro-spot 74 can be configured to have more or less homogeneity within a microchannel.

Figure 11:
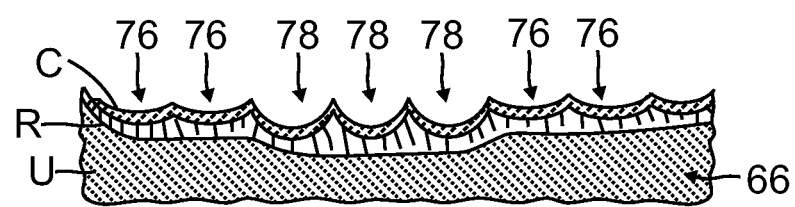
FIG. 11 is a cross-sectional illustration of a microchannel formed from a macro-spot having a varying distribution of energy levels and fluence.

Referring to FIG. 11, a cross-section of a microchannel 66 and spot impact in a portion of treated tissue is illustrated. The microchannel 66 has a homogeneous spot impact with contiguous ablated zones 76 and 78. The ablated zones 78 oriented at substantially the center of the microchannel 66 have greater depths than those ablated zones 76 oriented toward the margins and periphery of the microchannel 66. The patterning of depths is illustrative of a spot impact that may result from a macro-spot 42 and 44 having higher energy levels and fluence applied approximately about or along the center of the snail-shaped spot pattern in comparison to energy levels and fluence applied along marginal segments and the periphery of the pattern, as is illustrated in FIG. 5A. In effect, the higher energy levels and fluence substantially about or along the center of the macro-spot 42 and 44 destroy or vaporize tissue to greater depths along or about the center of the microchannel 66.

Figure 12A:
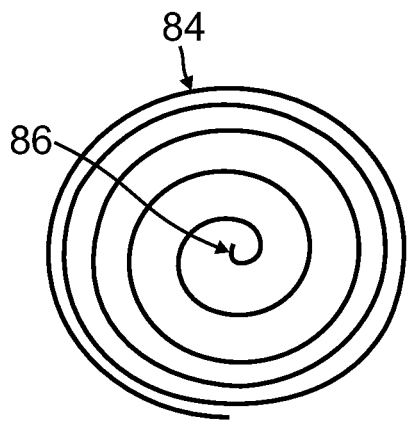
FIG. 12A is an illustration of a fractional pattern of a treatment macro-spot according to the invention.
Figure 12B:
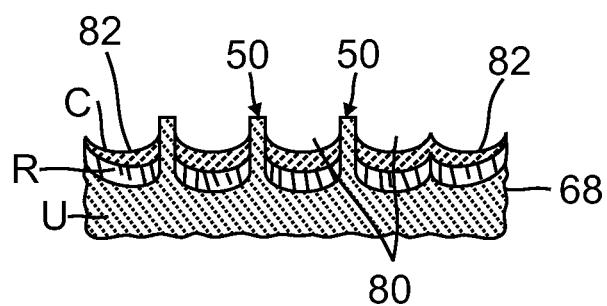
FIG. 12B is an illustration of a microchannel formed from a macro-spot having a varying density pattern as shown in FIG. 12A.

Referring to FIGS. 12A and 12B, a cross-section of a microchannel 68 and a spot impact in a portion of treated tissue are illustrated. The microchannel 68 has a non-homogeneous spot impact with undamaged tissue 50 between some of the ablated zones 80. The ablated zones 80 and 82 have substantially similar depths, but are either contiguous or non-contiguous with adjacent ablated zones as a result of the density or spread of the spiral scan line that forms the snail-shaped macro-spot 84. As shown in FIG. 12A, the macro-spot 84 is formed with gradually decreasing radii from the center 86 of the spiral scan line, such that, distances between successive spiral loops gradually decrease toward the macro-spot 84 periphery. The spot impact that results includes undamaged zones 50 of tissue between ablative zones 80 along the center of the microchannel 80 due to the larger radii and greater distances between successive spiral loops emanating from the spiral scan line center 86. The microchannel 80 also includes contiguous ablative zones 82 along the margins and periphery of the microchannel 68.

The microchannels 66 and 68 illustrated in FIG. 11 and FIG. 12B, respectively, illustrate only a few of a wide variety of possible configurations of microchannels that may result from variations in the spread and density of the spiral scan line of the snail-shaped macro-spot and from variations in the distribution of energy levels and fluence applied along the spiral scan line.

In other configurations of the microablative methods according to the invention, and the system 1 and/or laser unit 2 according to the invention, the $CO_2$ laser and the scanning device 30 may be configured additionally for deep fractional microablative treatments by which deep microchannels 6A, such as shown in FIG. 2, are created having depths and diameters of, for instance, up to about 1000 um and 120 um, respectively. In this configuration, the $CO_2$ laser and emitting device 3 may apply ablative radiation to treatment areas with two or more laser beam profiles, such that, micro-spot patterns and resulting arrays of deep microchannels 6A are combined with macro-spot 42 and 44 patterns and resulting large, superficial microchannels 62 and 64 to form a microablative pattern. Micro-spot and macro-spot patterns may be so combined in an unlimited manner. In addition, respective densities of the spot patterns may be controlled, and may be applied along treatment areas in random, overlapping or other patterns.

Software of the system 1 and/or laser unit 2 controls and designs the laser beam profiles by manipulating, for instance, beam power, to create arrays of single, deep microchannels 6A, 6B and 6C and patterns of homogeneous or non-homogeneous large, superficial microchannels 62 and 64 to achieve variable ablation depths and diameters and to thereby more precisely control treatment of subsurface tissue. Such flexibility in combining different laser beam profiles to produce two or more types of microchannels provides for customized beam profiles and thereby optimized microablative treatment protocols for a particular condition and pathology, as well as improved results per treatment session.

In one configuration, the method according to the invention initially scans a treatment area in a pulsed mode to form patterns of micro-spots with a given spot size, e.g., 120 um, to create an array of deep microchannels 6A while controlling the density of the spot patterns. Secondarily the method scans the same treatment area in a continuous wave mode to form patterns of macro-spots 42 and 44 with a given spot size, e.g., 700 um, to create a pattern of large, superficial microchannels 62 and 64 while controlling the density of the spot patterns. In another embodiment, this can be done simultaneously by a fast switching between pulsed mode and continuous mode so that in a single run the laser can embed microchannels in various desired locations while drilling a macrochannel. The combinations of micro and macro treatments spots, such as, for example, shown in FIGS. 3C and 3D, are unlimited and provide flexibility within in single $CO_2$ system in terms of control and adjustment of spot size, density, energy distribution, and other parameters discussed above. Microablative treatment patterns thereby may be readily controlled and adjusted in response to treatment demands.

Ablative Methods to Maintain Microchannels Open

Referring again to FIG. 1, current methods of microablation of tissue 5 often experience problems associated with the ability of microchannels 6 to retain their initial diameter (D) and/or depth (d) that result from application of ablation radiation to the surface of tissue. Microchannels 6 have a tendency to collapse mechanically and to fill with fluid. One solution to this problem is to freeze at least a portion of the tissue of the treatment area prior to applying ablation radiation. Freezing tissue helps tissue become relatively stiff and helps to block the flow of fluids into the microchannels.

In one aspect, the invention provides a method of patterning microchannels created in a treatment area and forming microchannels with different diameters and depths to achieve different functions within the microchannels and the surrounding tissue. The patterning of microchannels, and the differences between microchannels with respect to depth and diameter, help to achieve certain thermal effects and help to advantageously shrink and dry certain microchannels and associated surrounding tissues.

Referring again to FIG. 2, and with further reference to FIG. 1, the method of the invention ablates a treatment area 5 with laser radiation to create deep microchannels 6A and relatively more shallow or superficial microchannels 6B. The depth (d) and diameter (D) parameters of the microchannels 6A and 6B are controlled by the energy characteristics of the applied laser radiation. The deep microchannels 6A include a zone of ablation 6 having a certain depth (d) and diameter (D) and a zone of thermal damage 7 to the dermal tissue, e.g., "lethal damage" or "sublethal damage," resulting from the laser radiation. The relatively more shallow or superficial microchannels 6B have a certain depth (d) and diameter (D) to create a zone of coagulation 7 only within which no ablation occurs. Rather, the zone 7 experiences tissue coagulation that helps to shrink and to dry the superficial microchannel 6B and its surrounding tissue.

The invention is not limited to laser radiation and envisions that the method may employ coherent, non-ablative light in one or more different modalities, such as, for instance, a combination of treatment that may use one or more of RF, US, IPL or other coherent light.

Figure 13A:
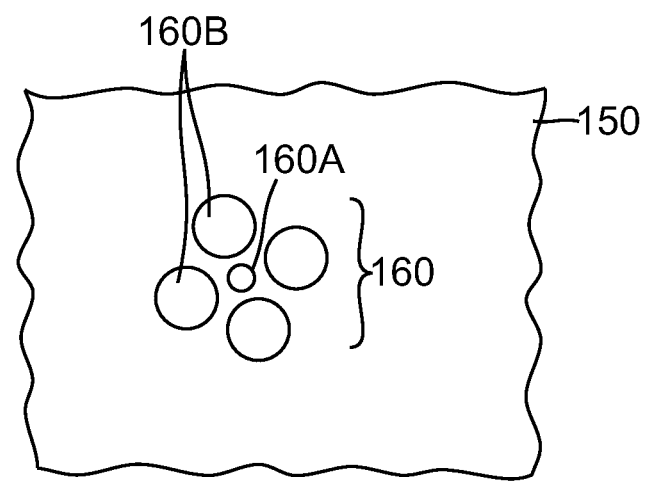
FIGS. 13A and 13B are illustrations of a microablation pattern of microchannels defining different diameters and depths according to the invention.

Referring to FIG. 13A, and with further reference to FIG. 2, the combination of deep and superficial microchannels 160A and 160B is created in the treatment area 5 in a pattern 160 whereby the deep microchannel 160A is surrounded by multiple superficial microchannels 160B, which may be referred to as a "flower pattern," wherein the deep microchannel 160A defines the flower center or stem and the multiple superficial microchannels 160B surround the deep microchannel 160B like "petals." As shown in FIG. 13A, a single deep microchannel 160A is surrounded by four superficial microchannels 160B. The invention is not limited in this respect and envisions that any number of superficial microchannels 160B may surround the deep microchannel 160A. In addition, the ratio of deep to superficial microchannels 160A and 160B may be varied. Further, the invention is not limited to the pattern 160 illustrated in FIG. 13A and anticipates that other configurations or patterns of deep microchannels 160A and superficial microchannels 160B are possible to achieve the functions of the patterning, as described in further detail below.

As a result of ablating the treatment area 150 with the pattern 160 of deep and superficial microchannels 160A and 160B, the coagulation effects resulting from ablation or formation of the superficial microchannels 160B help to shrink and to dehydrate the microchannel 160B and the surrounding tissue within the coagulation zone 7 of FIG. 1. The coagulation and drying of such surrounding tissue further helps to prevent flow of fluids into the microchannels 160A and 160B. Because of shrinking and drying of tissue within the coagulation zone 7, the superficial microchannel 160B and coagulation zone 7 stiffen and thereby serve as mechanical support to the adjacent deep microchannel 160A. The mechanical support that the stiffened superficial microchannels 160B and surrounding zones 7 lend to the deep microchannel 160A helps to prevent mechanical collapse of the deep microchannel 160A. The surrounding microchannels 160B and coagulation zones 7 thereby help the deep microchannel 160A remain open and relatively dry for a sufficient period of time after ablation to help to enable treatment and to help to enhance the effectiveness of such treatment.

Figure 13B:
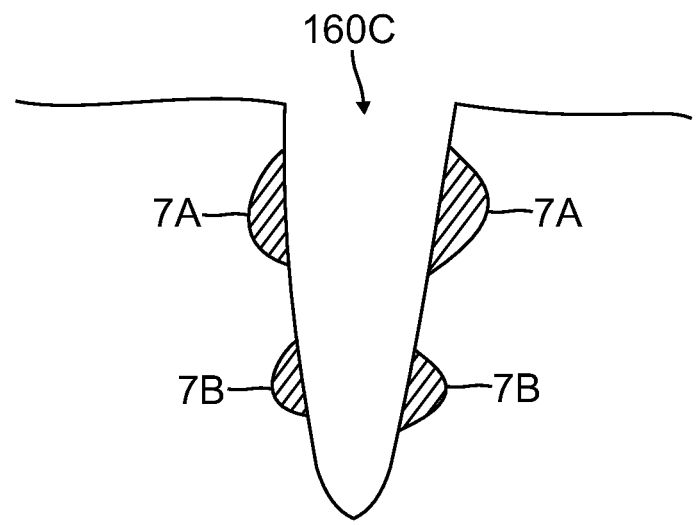

Referring to FIG. 13B, a cross-sectional illustration shows a microchannel 160C with coagulation areas or zones 7A and 7B formed along portions of walls of the microchannel 160C. Coagulation zones 7A and 7B may be formed during ablation that forms the microchannel 160C in a treatment area. Application of irradiation energy configured in accordance with one or more parameters applies to the skin or tissue of the treatment area and forms the microchannel 160C to an initial approximate desired or required depth; thereafter, irradiation energy applied to the treatment area may be altered or modified in accordance with one or more other or different parameters, such that, as a result, irradiation energy forms coagulation zones 7A, e.g., at or proximate to the initial approximate depth achieved, along portions of walls of the microchannel 160C as shown in FIG. 13B. Ablation may continue by irradiating energy configured in accordance with one or more parameters to continue formation of the microchannel 160C to a subsequent approximate depth that is relatively deeper than the initial approximate depth achieved. Irradiation energy configured with one or more other or different parameters may be applied that forms coagulation zones 7B, e.g., at or proximate to the subsequent approximate depth achieved, along portions of walls of the microchannel 160C. As shown in FIG. 13B, the coagulation zones 7A and 7B are defined at different depths of the microchannel 160C. The coagulation zones 7A and 7B along the microchannel 160C walls help to keep the microchannel 160C open once formed and help to prevent or at least minimize mechanical collapse of the microchannel 160C, thereby helping to provide mechanical stability to the microchannel 160C.

Figure 14:
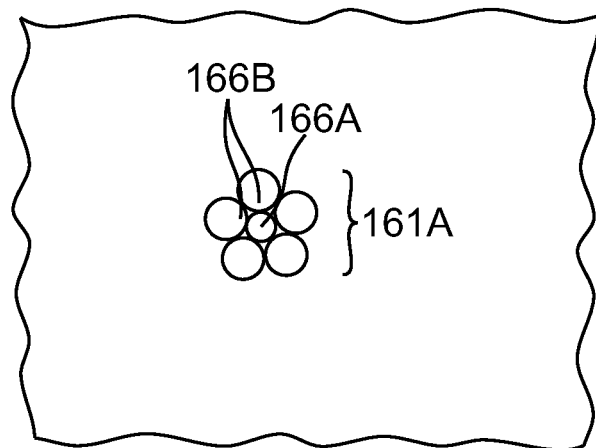
FIG. 14 is an illustration of another microablation pattern of microchannels according to the invention.

Referring to FIG. 14, the pattern of microchannels shown in FIG. 13 may include a pattern 161A whereby superficial microchannels 166B closely abut or are proximate to a deep microchannel 166A.

Figure 15:
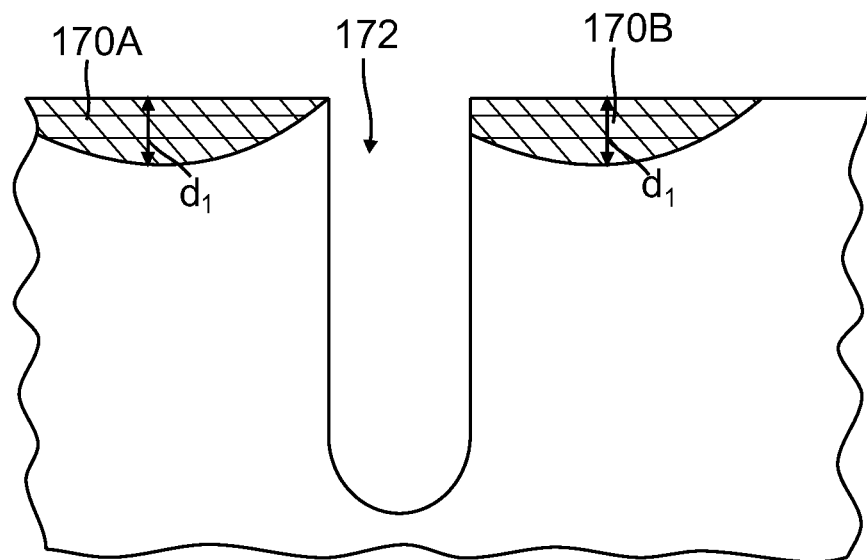
FIG. 15 is a cross-sectional illustration coagulation microchannels according to the invention.

Referring to FIG. 15, a schematic cross-sectional view illustrates an alternative configuration of the microchannels 160B of FIG. 13. In the configuration of FIG. 15, the microchannels 170A and 170B may define relatively shallow coagulation zones or holes that provide non-invasive, fractional treatment without creating the "microchannels" 160B of FIG. 13. For instance, the depth of such coagulation zones or holes may vary from about zero to about one-third a depth (d1) of a corresponding deep microchannel 172. Creating shallow coagulation zones or holes causes the thermally-affected tissue surrounding the zones or holes to stiffen. The shallow coagulation zones or holes also may serve as buffers or reservoirs to help collection of fluid before fluid flows into a deep microchannel 172.

Ultrasonic and Pressurized Systems to Maintain Open Microchannels

In another aspect, the apparatus includes a first energy application device to direct energy at tissue of a patient to cause at least one channel to be formed, a second energy application device to direct energy at the tissue of the patient to prevent the at least one channel from substantially closing, and a controller to control application of energy from the first energy application device to form the at least one channel, and control application of energy from the second energy application device to the at least one channel to prevent the at least one channel from substantially closing for at least a pre-determined interval of time.

Embodiments of the apparatus may include one or more of the following features.

The second energy application device may include a controllable energy application device to generate one or more standing waves over the at least one channel to elevate the Young modulus of the tissue.

The at least one channel may include a plurality of channels, and the controllable energy application device to generate the one or more standing waves may include a controllable energy application device to generate one or more standing waves having wavelengths based on a distance between at least two of the plurality of channels.

The second energy application device may include a fluid source, and a pump to pump pressurized fluid from the fluid source towards the at least one channel.

The pump may further be configured to create a vacuum external to the at least one channel to remove at least some of the fluid that was directed into the at least one channel.

The fluid of the fluid source may include one or more of, for example, gas, enhancing fluid to enhance the effect of laser energy transmitted through the pressurized enhancing fluid, and/or medicinal fluid.

The second energy application device may include a controllable ultrasound device to apply ultrasound energy in a direction parallel to a longitudinal axis of the at least one channel to generate standing waves of varying amplitude to cause varying elasticity levels of the tissue.

In another aspect, a method is disclosed. The method includes forming at least one channel in a tissue of a patient, and applying energy to the at least one channel to prevent the at least one channel from substantially closing for at least a pre-determined interval of time.

Embodiments of the method may include any one of the features described above in relation to the apparatus, as well as one or more of the following features.

Applying the energy may include generating one or more standing waves over the at least one channel to elevate the Young modulus of the tissue.

The at least one channel may include a plurality of channels, and generating the one or more standing waves may include generating one or more standing waves having wavelengths based on a distance between at least two of the plurality of channels.

The one or more standing waves may include troughs located approximately at a halfway point between the at least two of the plurality of channels.

Generating the one or more standing waves having wavelengths based on the distance between at least two of the plurality of channels may include generating one or more standing waves having wavelengths equal to an integer multiple, n, of the distance between the at least two of the plurality of channels.

Generating the one or more standing waves may include generating one or more ultrasound standing waves.

Applying the energy may include applying ultrasound energy in a direction parallel to a longitudinal axis of the at least one channel to generate standing waves of varying amplitude to cause varying elasticity levels of the tissue.

Applying the energy may include directing pressurized fluid into the at least one channel.

The pressurized fluid may include one or more of, for example, pressurized gas, pressurized enhancing fluid to enhance the effect of laser energy transmitted through the pressurized enhancing fluid, and/or pressurized medicinal fluid.

Directing the pressurized fluid may include directing the pressurized fluid at a pre-determined time interval following the application of energy to form the at least one channel.

The method may further include removing at least some of the fluid occupying the at least one channel by creating a vacuum externally to the at least one channel.

Forming the at least one channel may include forming at least one channel having pre-determined dimensions in the tissue, and a respective thermally affected thermal zone having a pre-determined configuration profile, the thermal zone extending away from the at least one channel.

Disclosed herein are apparatus, systems, methods and devices, including an apparatus for treating tissue that includes a first energy application device to direct energy at tissue of a patient to cause at least one channel to be formed, a second energy application device to direct energy at the tissue of the patient to prevent the at least one channel from substantially closing, and a controller to control application of energy from the first energy application device to form the at least one channel, and control application of energy from the second energy application device to the at least one channel to prevent the at least one channel from substantially closing for at least a pre-determined interval of time. In some embodiments, the second energy application device may include a controllable ultrasound device to apply ultrasound energy in a direction parallel to a longitudinal axis of the at least one channel to generate standing waves of varying amplitude to cause varying elasticity levels of the tissue. In some embodiments, the second energy application device may include a fluid source, and a pump to provide pressurized fluid from the fluid source towards the at least one channel.

Hole (or channel) formation in the tissue of a person may be performed, in some embodiments, through microablation procedures by, for example, applying electromagnetic radiation to the tissue for ablating a channel therein having a (predetermined) width and predetermined depth. In some embodiments, the procedure includes non-ablatively heating tissue on the bottom of the channel with electromagnetic radiation and creating a thermal affected zone of predetermined volume proximate said channel. Suitable radiation generating devices that may be used in forming microchannels through microablation include, for example, a CO2 laser device, an Er:YAG laser device, a Tm:YAG laser device, a Tm fiber laser devices, an Er fiber laser device, a Ho fiber laser device, and/or other types of laser devices. Other types of radiation or energy sources may also be used. A schematic diagram of an apparatus to perform microablation to form microchannels is provided in FIG. 16. Briefly, the apparatus depicted in FIG. 16 may include a laser unit 200 and a laser emitting device 203 for ablating a microchannel 206 into a tissue 205, for example, for applying a treatment thereto. The microchannel 206 may be, e.g., a column, a well, a hole, or the like, created in the tissue 205 by ablating the tissue 205 by the laser emitting device 203 and the laser beam 204. Microablation of the tissue 205 may result in ablation of the microchannel. Microablation of the tissue may also result in dissipation of heat from the heated and evaporated tissue by the tissue surrounding the resultant microchannel 206. Thus, ablation of the tissue 205, producing the microchannel 206, may result in a thermal affected zone 207 surrounding the walls and/or bottom of the microchannel 206.

In some embodiments, hole stabilization mechanisms may be based on use of an ultrasound device 208 with the laser emitting device 203. The ultrasound generator—208 generates standing waves along the skin's plane, which is perpendicular to the main axis of the holes, in order to elevate the effective Young Modulus of the tissue and make it more rigid. The more rigid the tissue around the holes is, the less it tends to collapse and block the hole. A standing wave creates "stationary" crests and troughs. The distance between them is proportioned to the wavelength. Assuming a certain hole's distribution (distance between holes), one can choose a certain wavelength/s that localize/s these crests and troughs on the holes or in between the holes. One option would be to use a wavelength which is equal to the distance between the holes and to apply the ultrasound in such a relative geometry that the crests will be in the middle between holes.

Figure 16:
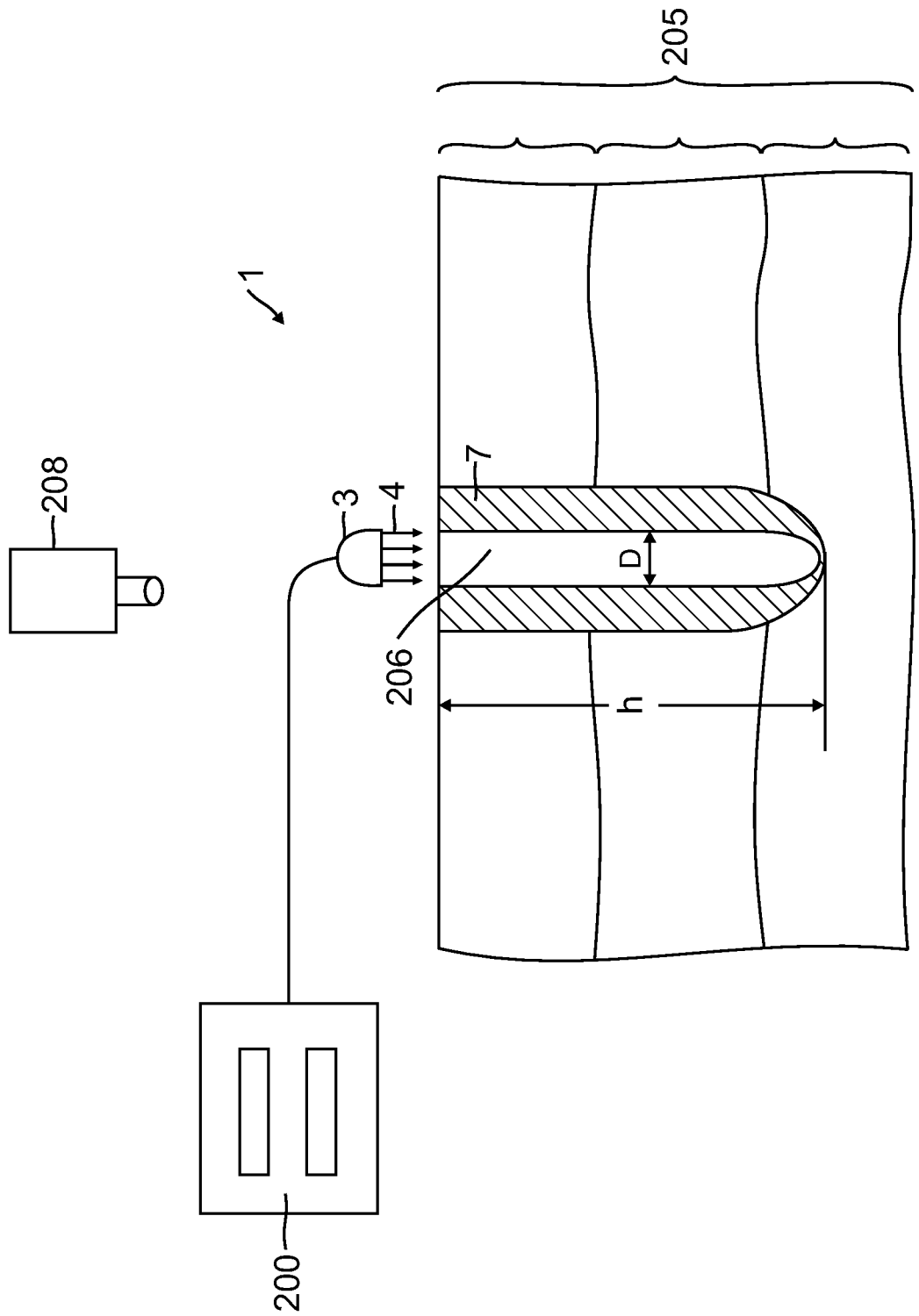
FIG. 16 is a schematic diagram of an apparatus used for hole formation and for maintaining holes (channels) open.

Ultrasound energy may be generated, in some embodiments, using an ultrasound generator, such as the ultrasound generator 208 depicted in FIG. 16. In some implementations, the generator 208 may be a contact generator, in which the generator is mechanically coupled to the tissue (e.g., via a coupling layer such as a suitable fluid couplant), and causes resultant waves (acoustic waves) through mechanical excitation. Suitable contact-based generators may include, for example, an ultrasonic wheel generator (i.e., a moveable generator displaced over the object), an ultrasonic sled generator, and/or a water-coupled generator. These types of generators may include an ultrasonic transducer implemented, for example, using a piezoelectric element, or some other vibrating transducer, that mechanically oscillates at frequencies controllable by regulating the voltage/current applied to the piezoelectric element. In some implementations, the generator 208 may be a non-contact generator, i.e., the generator is not in direct mechanical contact with the object to be inspected. A suitable non-contact generator may be an air-coupled transducer that includes a mechanical vibrating transducer (e.g., such as a piezoelectric element) that can controllably oscillate to produce the ultrasonic waves applied to the object. The output port of such a generator is placed proximate to the object (e.g., the tissue), and emitted ultrasonic wave are directed to the object at the application point via an air barrier separating the output port of the generator and the object.

Other types and/or implementations of generators to cause waves (ultrasonic waves or other types of waves) may also be used.

In some embodiments, another implementation for hole stabilization is to use using any wavelength with an integer ratio to the distance between holes. Such an implementation can be done on symmetric hole pattern (matrix) of statistically on a randomized holes distribution.

In some embodiments, hole stabilization can be achieved by a "pushing" mechanism. Specifically, low amplitude high resolution ultrasound is used today with femtosecond lasers to displace bubbles during the treatment of human eye lenses. Using ultrasound for transdermal drug delivery is also known. A similar mechanism may thus be used to push material through the holes once they are open. This requires an ultrasound application (e.g., substantially simultaneously) along the hole's main axis perpendicular to the skin surface.

In some embodiments, application of ultrasound energy may be used to help material, like fat, which is ablated at the bottom of the hole, to be evacuated through the hole (or channel). To perform such material evacuation, vibrations along the hole's walls are caused. One way to do that is by changing the amplitude of the standing waves. Under the assumption that a standing wave will change the tissue elasticity, then a "pulsating" elasticity (slightly changed elasticity) will result in small movements of the hole's wall. This will help the material being evacuated to travel in either direction, e.g., in and out. If a certain pressure gradient can also be applied by external vacuum, skin stretching, or traveling waves along the hole's wall, then one can control the direction and enhance the evacuation of material from the bottom of the hole.

Figure 17A:
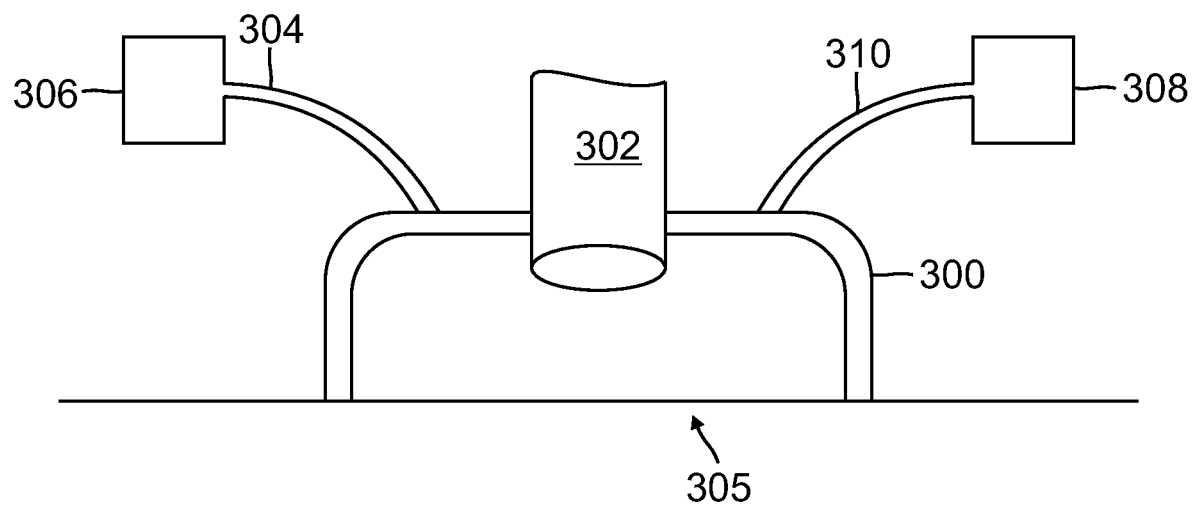
FIGS. 17A-17B are schematic diagrams of an apparatus used for supplying and removing pressurized fluids.
Figure 17B:
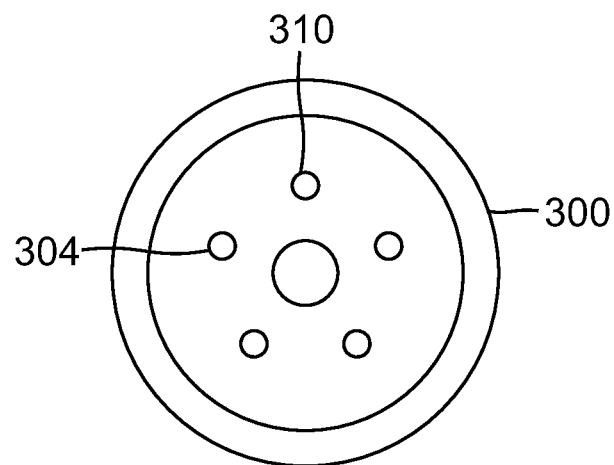

In some implementations, channel stabilization may be achieved by using a pressurized fluid, e.g., gas or liquid, to keep open the holes created by, for example, a CO2 fractional laser in order to allow a second "shot" with the bottom of the hole still open. Such implementations include a mechanism comprising an adapter 300 that fits on the end portion of the laser 302 as illustrated in FIGS. 17A and 17B. In such implementations, a vacuum tube 304 with sourced vacuum 306 is attached to the adapter 300, and a high pressure pump 308 and the 310 coupled to the adapter (e.g., at its other end) introduce a fluid into the adapter, for example, just prior to activation of the laser. As illustrated in FIG. 17B, tube 304 and 310 which carry vacuum and pressurized fluid(s) may have a plurality of ports within the adapter to allow rapid introduction and evacuation of fluids. In some embodiments, the fluid could be a material which enhances the ability of the first laser firing to achieve its desired depth and includes medicinal and/or anesthetic substances.

In operation, the adapter 300 is placed in contact with the skin 305 as shown in FIG. 17A and pressure applied. A pre-trigger mechanism forces pressure and fluid into the adapter, and then the laser 302 is then fired. The fluid migrates into the hole 206 waiting for the second firing (or other treatment). Then the adapter can be removed or even the vacuum pump activated to remove the fluid into the adapter's tube. Instead of a separate vacuum and pressure source, a single mechanism to perform both functions, such as a reversible pump, may be used. The foregoing pressurized system may be used instead of the application of ultrasound energy or together with the application of ultrasonic energy.

An additional advantage is that use of the pressure should also serve to reduce pain to the patient. Under the "Gate Theory" of pain management, if the skin is put under pressure (e.g., vacuum or positive pressure on my part), the brain is tricked into feeling the pressure and not the pain of the holes being drilled into one's skin (this is predicated on a concept similar to that implemented in the commercially-available ShotBlocker® device which is a pressure plate placed around an injection site). When used the pressure on the skin makes the patient "forget" about the injection pain.

Control of Laser Treatment Spots

Figure 18:
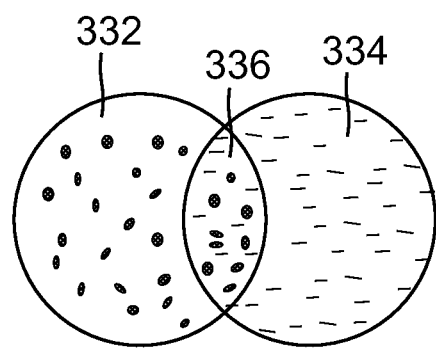
FIG. 18 is a schematic illustration of different types of patterns of microchannels or treatments "spots" resulting from microablation treatment.

Referring to FIG. 18, the laser unit of FIG. 1, for example, may deliver the laser beam in a first predetermined pattern 332 of treatment spots or in a second predetermined pattern of treatment spots 334. Alternatively, the laser unit may modify the laser beam during the course of a single treatment to deliver both the first and the second predetermined patterns 332 and 334 of treatment spots producing an area of overlaid patterns 336 along the surface of the tissue.

The scanner 30 of FIG. 1 and software according to the invention enables the laser emitting device 3 of FIG. 1 to deliver a laser beam to the surface of tissue in one or more predetermined patterns of treatment spots, as described with reference to FIG. 18, while randomizing the sequence of treatment spots applied to the tissue surface. The treatment spots are randomized across a given treatment area because of the movement of the scanner, as shown by arrow 40 in FIG. 1, across the treatment area. While the laser emitting device 3 emits the laser beam, the movement of the scanner across the treatment area in effect randomizes or "spreads" the predetermined pattern across the treatment area. As a result, the density and distribution of the treatment spots in the given area are random. The scanner 30 may be moved repeatedly across the given treatment area such that an overlap of treatment spots is produced which thereby results in greater spot density and distribution. In addition, the movement of the scanner 30 permits treatment of a relatively large treatment area and effectively scans or "brushes" the tissue surface with treatment spots. Repetitive scans or brushes results in varying densities and distribution of treatment spots across the given treatment area that is a function of the number of brushes and the overlap between each brush across the treatment area.

Figure 19:
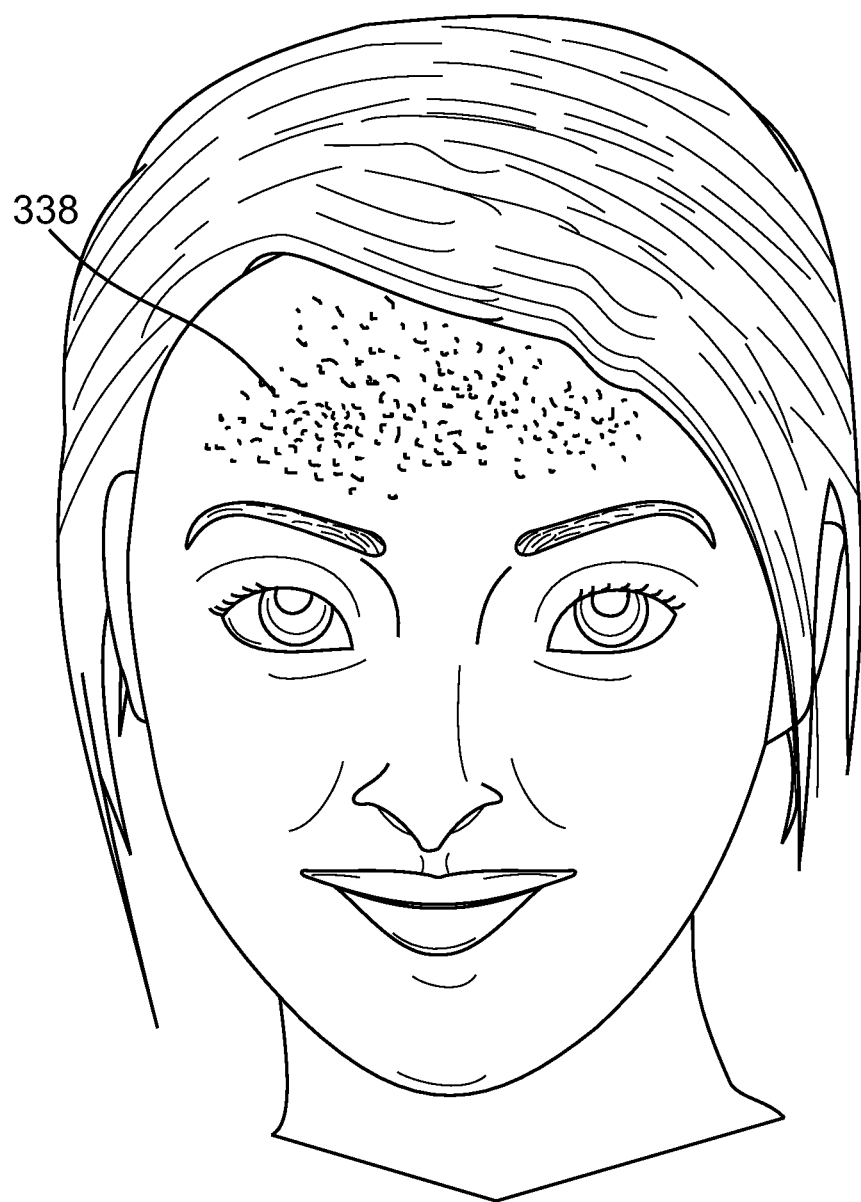
FIG. 19 is a schematic illustration of varying distribution and density of treatment spots in a given treatment area as a result of microablation treatment controlled by the scanner and software according to the invention.

Referring to FIG. 19, a facial image illustrates multiple treatment spots 338 randomly distributed across a treatment area with varying spot densities at certain areas within the treatment area. As shown in FIG. 19, by way of example, the density of treatment spots may be greater in the middle section of the forehead, an area typically in which wrinkles may be present. However, density treatment may be varied from that shown in FIG. 19 according to a particular patient's needs. Random distribution and varying density of treatment spots 338 results, as mentioned, from the scanner 30 moving across the treatment area to deliver multiple scans or brushes as well as overlaying scans or brushes. The scanner and software according to the invention thereby enable greater control of treatment spots in terms of distribution and density of treatment spots. An operator, such as a physician, may thereby distribute or "spread" treatment spots in a controlled and intuitive manner whereby the operator would scan a particular area of surface tissue with greater density, but scan another area with less density, depending upon the tissue and the treatment desired. For instance, certain areas may be scanned or brushed repeatedly due to different skin characteristics in terms of pigmentation, elasticity, distance to bones, etc. Other areas may receive less treatment and, therefore, have less spot density and/or have a gradual decrease or phasing out of spot density, such as along the boundaries between treatment areas and the eyes, lips, and hair.

In one embodiment, instead of the treatment spots being all of either type, 6A or 6B as in FIG. 2, the treatment spots may be mixed and matched so that a user-selectable proportion of 6A type and 6B type treatment spots are delivered to the patient's skin. For example, the treatment spots may be a mixture to form a plurality of spots 160 as shown in FIG. 13 and their relative spacing to one another controlled by the physician.

In addition, the scanner may incorporate speed-sensing or distance-sensing technology so that the software can deliver predetermined density of spots to an area of the patient's skin, irrespective of the speed with which the physician moves the scanner over the patient's skin.

Also, under control of the physician, the scanner's software may provide treatment spots like the FIG. 2 type, but in some areas of the patient's skin only and may provide FIG. 2 type 6B in other areas of the skin, depending on the patient's skin characteristics such as skin elasticity, pigmentation, closeness to hairlines or the eyes, etc.

The foregoing skin treatment is in context to the known "step and shoot" treatment in which the scanner is placed over a spot of skin, then laser activated and then the scanner is moved to the next adjacent untreated area of the patient's skin.

The somewhat random scanning sequences described above may also assist in lowering overall patient pain as the scanner moves when firing the laser, then spreading the treatment spots of a broader area than with the traditional "step and shoot" method. The software may program the scanner to disallow two consecutive firings at predetermined distances from one another.

In another embodiment of the invention, the software the scanner 30 employs to define the laser beam profile controls the scanning speed or speed of delivery of the treatment beam with respect to the speed with which a physician scans or brushes the treatment area. In one embodiment of the invention, the software correlates the scanning speed to the speed of the movement that the physician uses to scan or brush the treatment area. Correlating scan speed and speed of movement of the scanner helps to ensure application of a certain homogeneous distribution of treatment spots irrespective of the speed the physician uses to scan or brush the tissue surface.

In another embodiment, the scanner and software according to the invention are configured to apply two or more predetermined patterns of treatment spots, such as shown in FIG. 18. As a result, a dynamic distribution of different treatment spots having different tissue effects, as can be seen in the depth D of the microchannels 6A and 6B of FIG. 2, is created in the dermal layer. The software according to the invention allows selection and control of the different types of treatment spots or microchannels 6A and 6B. Such selection and control are achieved with at least the selection and control of the pulse width, the energy fluence, the pulse repetition rate, and any combination of these parameters, to create different treatment spots and to enable the scanner to emit laser energy that creates different treatment spots in a given treatment area. In addition, the software according to the invention will enable the selection and control of the ratio of two of more different treatment spots that are applied to the given treatment area.

FIGS. 2 and 18 illustrate two different types of spots or microchannels 6A and 6B and two different predetermined patterns of their application. The scanner 30 and software according to the invention may create these different predetermined patterns in a randomized sequence to produce a varying distribution and density of treatment spots within a treatment area. The invention, however, is not limited in this respect and envisions the software will permit the selection and control of a number of different types of spots or microchannels and any of a variety of spot patterns.

The software according to the invention enables the scanner 30 to achieve multi-levels of penetration of the dermal layer. This enables a physician to tailor and to customize the microablation treatment in accordance with a patient's skin pathologies and pigmentation and to deliver optimal and highly customized microablation to a single treatment area.

In a further embodiment of the invention, the scanner 30 and software according to the invention permits the selection and control of predetermined patterns of treatment spots that are not homogenous. For instance, a pattern may produce a high density of treatment spots at and proximate to a center of the pattern, while producing a relatively low density of treatment spots at the periphery of the pattern. Combining capabilities of selection and control of different non-homogeneous treatment patterns and their densities and distributions in a given treatment area, the invention provides a physician with an ability to treat different skin characteristics simultaneously, a capability to vary depths of ablation, and a technique to accommodate the boundaries between treatment and non-treatment areas, such as eyes, lips, and hair. The software in effect allows repeated scanning or brushing, while applying precisely required or desired treatment spot densities.

Description of Foot Activated Control

Referring to FIG. 20, in one aspect, the invention provides a foot-activated control (entitled herein a footswitch) 410 that is constructed and arranged for use in controlling and, more particularly, in actuating a light-based system or device. The footswitch 410 includes at least one electrical cable 413 to couple the footswitch 410 operatively to the light-based system or device. Such light-based system or device is configured for emission of laser and/or other coherent light applied in accordance with ablation methods to the surface of tissue for various treatments.

The footswitch 410 includes a pedal 412 having, in one configuration, a substantially planar surface and sufficient area 412A to receive at least a portion of an operator's foot. The pedal 412 is actuated or activated, e.g., depressed, by the operator's foot on the surface 412A. In this manner, the footswitch 410 serves as an accelerator to increase or to decrease the firing of the light-based system or device, such that, the system or device increases or decreases, e.g., the duration of, the emission ablation treatment radiation. For example, the footswitch 410 may be useful in connection with controlling the density and depth of treatment spots 338 in FIG. 19.

In one configuration of the invention, the footswitch 410 is constructed and arranged as a "smart" pedal 412 that provides a dynamic range of control of one or more parameters of the tissue ablation treatment, including, but not limited to, repetition rate, light energy, light penetration, light depth, treatment spot size, spot density, repetition rate, etc. Each parameter may be associated with a sensor 414A, 414B, 414C, and 414D that is integrated with the footswitch 410 and, for instance, is disposed below an outer sheath covering the surface 412A of the pedal 412 (as shown in dashed lines in FIG. 20). The operator may thereby control dynamically, during treatment, one or more parameters by actuating with their foot one or more sensors 414A, 414B, 414C, and 414D, alone or in any combination. FIG. 20 shows four sensors and a particular arrangement of the sensors 414A, 414B, 414C, and 414D on the pedal 412. The invention, however, is not limited in this respect and envisions that any number of sensors may be incorporated with the pedal 12 and in any of a variety of configurations and arrangements.

Referring to FIG. 21 and with further reference to FIG. 20, the footswitch 410 may be operatively coupled with a user interface 416 that enables the operator to select various modes of operation of and parameters for actuation by the footswitch 410. The interface 416 may include a visual display 417 of the modes 417A and the parameters 417B that the footswitch 410 may control. Such modes and parameters 417A and 417B may be selected and activated for control by the footswitch 410 by, for instance, touch-screen software. In one configuration, the interface 416 may be incorporated with the light-based system or device to which the footswitch 410 is coupled operatively. Alternatively, or additionally, the interface 416 may be a peripheral device that is configured to operate alone or in conjunction with a controller, which is operatively coupled with the light-based system or device.

The invention further includes any software, hardware, and firmware, and associated electronics, that are required to operate and to provide control of the footswitch 410, the sensors 414A, 414B, 414C, and 414D, and the interface 16, and that are required to integrate the footswitch 10 and the interface 16 with a light-based system or device and/or a controller.

Having thus described at least one illustrative aspect of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method of treating human skin tissue with a micro ablation treatment, comprising:
   providing a first energy application device that is configured to direct energy at the skin tissue of a patient to cause at least one micro ablation channel to be formed in the skin tissue; and
   providing a controller configured to:
   control application of energy from the first energy application device to form the at least one micro ablation channel in the skin tissue;
   the method comprising:
   applying, under the control of the controller, energy from the first energy application device to form a vertically-disposed central micro ablation channel having a depth d1 in the skin tissue; and
   applying, under the control of the controller, energy from the first energy application device to form more than one secondary micro ablation channels, each having a depth up to one third of the depth d1, in the skin surrounding the central micro ablation channel, whereby the secondary micro ablation channels shrink and dehydrate thereby stiffening and serving as a mechanical support to the central micro ablation channel to keep it open for a time period sufficient for the treatment.

2. The method of claim 1 further comprising the step of the controller causing the energy application device to form the secondary micro ablation channels so that they are spaced a predetermined distance from the central micro ablation channel.

3. The apparatus of claim 1 further comprising the step of the controller causing the energy application device to form the secondary micro ablation channels so that they abut a periphery of the central micro ablation channel.

4. The apparatus of claim 1 further comprising the step of the controller causing the energy application device to form the central micro ablation channel and the secondary micro ablation channels having the same diameter.

5. The apparatus of claim 1, further comprising the step of the controller causing the energy application device to form the central micro ablation channel with a first diameter smaller than a second diameter of the secondary micro ablation channels.

6. The apparatus of claim 1, further comprising the step of the controller causing the energy application device to form the secondary micro ablation channels as coagulation zones causing the surrounding tissue to stiffen.

* * * * *